(12) United States Patent
Tagami et al.

(10) Patent No.: US 11,500,129 B2
(45) Date of Patent: Nov. 15, 2022

(54) OPTICAL ELEMENT, MATERIAL, OPTICAL APPARATUS AND COMPOUND

(71) Applicant: CANON KABUSHIKI KAISHA, Tokyo (JP)

(72) Inventors: Kei Tagami, Yokohama (JP); Terunobu Saitoh, Hachioji (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 360 days.

(21) Appl. No.: 16/574,708

(22) Filed: Sep. 18, 2019

(65) Prior Publication Data
US 2020/0012014 A1   Jan. 9, 2020

Related U.S. Application Data

(63) Continuation of application No. PCT/JP2018/012145, filed on Mar. 26, 2018.

(30) Foreign Application Priority Data

Mar. 28, 2017   (JP) .............................. JP2017-063817
Mar. 6, 2018   (JP) .............................. JP2018-040129

(51) Int. Cl.
    *C08L 79/02*   (2006.01)
    *G02B 1/04*   (2006.01)

(52) U.S. Cl.
    CPC .............. *G02B 1/041* (2013.01); *C08L 79/02* (2013.01)

(58) Field of Classification Search
    CPC ........... G02B 1/041; G02B 1/04; C08L 79/02; C07C 2603/18; C07C 217/76;
    (Continued)

(56) References Cited

U.S. PATENT DOCUMENTS 6,017,644 A   1/2000   Toshida et al.
6,180,303 B1   1/2001   Uematsu et al.
(Continued)

FOREIGN PATENT DOCUMENTS

CN   103242174 A   8/2013
JP   11-092442 A   4/1999
(Continued)

OTHER PUBLICATIONS

International Preliminary Report on Patentability in International Application No. PCT/JP2018/012145 (dated Oct. 2019).
(Continued)

*Primary Examiner* — Balram T Parbadia
(74) *Attorney, Agent, or Firm* — Venable LLP

(57) ABSTRACT

The triarylamine compound is represented by the following general formula (1), and the material, the optical element, and the optical apparatus each include a polymerized product (cured product) of the triarylamine compound.

(Continued)

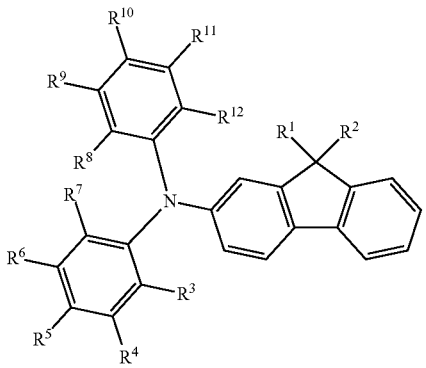

(1)

(In the general formula (1), $R^1$ and $R^2$ are each independently selected from a substituted or unsubstituted alkyl group having 1 to 10 carbon atoms, and a substituted or unsubstituted alkylene group having 1 to 8 carbon atoms, the alkylene group having a polymerizable functional group, and $R^3$ to $R^{12}$ are each independently selected from a hydrogen atom, a cyano group, a trifluoromethyl group, a substituted or unsubstituted alkyl group, a substituted or unsubstituted alkylene group having a polymerizable functional group, and a polymerizable functional group, provided that at least one of $R^3$ to $R^{12}$ represents an electron-withdrawing group, and at least one of $R^1$ to $R^{12}$ has a polymerizable functional group.)

15 Claims, 2 Drawing Sheets

(58) Field of Classification Search
CPC ... C07C 217/92; C07C 219/32; C07C 219/34; C07C 255/58; C07C 255/59; C07D 303/22; C07D 303/23; G08F 20/34
See application file for complete search history.

(56) References Cited

U.S. PATENT DOCUMENTS

| | | |
|---|---|---|
| 7,001,708 B1 | 2/2006 | Belfield |
| 7,258,822 B2 | 8/2007 | Yamaguchi et al. |
| 7,364,824 B2 | 4/2008 | Kikuchi et al. |
| 7,563,553 B2 | 7/2009 | Kikuchi et al. |
| 8,829,230 B2 | 9/2014 | Saitoh |
| 9,181,474 B2 | 11/2015 | Kim et al. |
| 9,718,764 B2 | 8/2017 | Stoessel et al. |
| 9,882,143 B2 | 1/2018 | Kim et al. |
| RE47,000 E | 8/2018 | Saitoh |
| RE47,556 E | 8/2019 | Saitoh |
| 10,407,384 B2 | 9/2019 | Stoessel et al. |
| 2004/0043312 A1 | 3/2004 | Kikuchi et al. |
| 2006/0029870 A1 | 2/2006 | Nukada et al. |
| 2007/0111029 A1* | 5/2007 | Yamada ............... H01L 51/5036 564/429 |
| 2007/0240756 A1* | 10/2007 | Lee ........................ C09B 57/02 549/60 |
| 2013/0137023 A1* | 5/2013 | Watariguchi ............ G03G 5/14 430/57.1 |
| 2014/0042411 A1* | 2/2014 | Fukuzaki ................ C07B 63/00 548/440 |
| 2014/0332772 A1 | 11/2014 | Han et al. |
| 2018/0277761 A1* | 9/2018 | Hayashi ................ C07F 7/0812 |
| 2018/0331298 A1* | 11/2018 | Hayashi ............... C07D 401/10 |
| 2019/0006596 A1* | 1/2019 | Hayashi ............... H01L 51/0054 |

FOREIGN PATENT DOCUMENTS

| | | |
|---|---|---|
| JP | 2000-066425 A | 3/2000 |
| JP | 2005-227368 A | 8/2005 |
| JP | 2006-058822 A | 3/2006 |
| JP | 2006-072293 A | 3/2006 |
| JP | 2006-085043 A | 3/2006 |
| JP | 2006-232907 A | 9/2006 |
| JP | 2007-011320 A | 1/2007 |
| JP | 2007-086522 A | 4/2007 |
| JP | 2008-165248 A | 7/2008 |
| JP | 2008-186717 A | 8/2008 |
| JP | 2010-091851 A | 4/2010 |
| JP | 2012-167019 A | 9/2012 |
| JP | 2016-516084 A | 6/2016 |
| WO | 2018/181183 A1 | 10/2018 |

OTHER PUBLICATIONS

International Search Report in International Application No. PCT/JP2018/012145 (dated Jun. 12, 2018).
Extended European Search Report In European Application No. 18776675.3 (dated Nov. 2020).
Ningwei Sun et al., "Novel Aromatic Polyamides Containing 2-Diphenylamino-(9,9-dimethylamine) Units as Multicolored Electrochromic and High-Contrast Electrofluorescent Materials," 55 J. Polym. Sci., Part A: Polym. Chem. 213-222 (Oct. 2016).
First Office Action in Chinese Application No. 201880020566.7 (dated Sep. 2022).

* cited by examiner

OPTICAL ELEMENT, MATERIAL, OPTICAL APPARATUS AND COMPOUND

CROSS-REFERENCE TO RELATED APPLICATIONS

This application is a Continuation of International Patent Application No. PCT/JP2018/012145, filed Mar. 26, 2018, which claims the benefit of Japanese Patent Application No. 2017-063817, filed Mar. 28, 2017, and Japanese Patent Application No. 2018-040129, filed Mar. 6, 2018, all of which are hereby incorporated by reference herein in their entirety.

BACKGROUND OF THE INVENTION

Field of the Invention

The present invention relates to an optical element, a material, an optical apparatus, and a compound, and more particularly, to a triarylamine compound, a material, an optical element, and an optical apparatus each having a characteristic in that a dispersion characteristic (Abbe number (vd)) of refractive indices is high and a secondary dispersion characteristic ($\theta g,F$) thereof is high (high $\theta g,F$).

Description of the Related Art

In general, the refractive index of an optical material, such as a glass material or an organic resin, gradually increases as the wavelength of light to be refracted by the material becomes shorter. Indicators each representing the wavelength dispersibility of the refractive index are, for example, an Abbe number (vd) and a secondary dispersion characteristic ($\theta g,F$). The Abbe number and the $\theta g,F$ value are values peculiar to each optical material, but in many cases, the values each fall within a certain range. A relationship between the secondary dispersion characteristic and Abbe number of each of conventional optical materials (a glass material and an organic resin) is shown in FIG. 1.

The Abbe number (vd) and the secondary dispersion characteristic ($\theta g,F$) are represented by the following equations:

$$\text{Abbe number } [vd]=(nd-1)/(nF-nC)$$

$$\text{Secondary dispersion characteristic } [\theta g,F]=(ng-nF)/(nF-nC)$$

where nd represents a refractive index at a wavelength of 587.6 nm, nF represents a refractive index at a wavelength of 486.1 nm, nC represents a refractive index at a wavelength of 656.3 nm, and ng represents a refractive index at a wavelength of 435.8 nm.

However, an optical material having a high $\theta g,F$ characteristic deviating from a value in the certain range has also been synthesized by designing the configuration (material kind or molecular structure) of an optical material (e.g., a glass material or an organic resin) in detail. For example, polyvinyl carbazole (positioned at a point A in FIG. 1) serving as an organic resin has a $\theta g,F$ characteristic higher than that of a general-purpose organic resin material.

In general, in a refracting optical system, a chromatic aberration is reduced by combining glass materials having different dispersion characteristics. In, for example, the objective lens of a telescope or the like, a chromatic aberration appearing on its optical axis is corrected by using the following materials in combination: a glass material having small dispersion is used as a positive lens, and a glass material having large dispersion is used as a negative lens. Accordingly, for example, when the configurations and number of lenses are limited, or when glass materials to be used are limited, it may become extremely difficult to sufficiently correct the chromatic aberration. As one method of solving such problem, the design of optical elements involving exploiting a glass material having an abnormal dispersion characteristic has been performed.

In addition, when an optical element that is excellent in chromatic aberration-correction function and has, for example, an aspherical shape is produced, a method involving, for example, molding an organic resin on a spherical glass or the like has the following advantage over a method involving using a glass material as a material: mass productivity, moldability, degree of freedom in shape, and light-weight property are excellent. However, the optical characteristic of a conventional organic resin falls within a certain limited range as shown in FIG. 1, and hence the number of organic resins showing specific dispersion characteristics is extremely small.

In Japanese Patent Application Laid-Open No. 2012-167019, there is a report that a sulfone (meth)acrylate serving as an organic material positioned at the point A in FIG. 1 has a higher secondary dispersion characteristic (higher $\theta g,F$ characteristic) than that of a general-purpose organic material.

Meanwhile, a triarylamine compound has been widely utilized in, for example, an electrophotographic photosensitive member, an organic electronics material, and an organic nonlinear optical material. In Japanese Patent Application Laid-Open No. 2007-011320, there is a proposal of a triarylamine compound as a charge-transportable compound to be used in the outermost surface layer of an electrophotographic photosensitive member. In Japanese Patent Application Laid-Open No. 2005-227368, there is a proposal of a triarylamine compound as an organic compound having nonlinear optical activity to be dispersed in a polymer binder.

The material proposed in Japanese Patent Application Laid-Open No. 2012-167019 has a high secondary dispersion characteristic (high $\theta g,F$ characteristic), but a higher $\theta g,F$ characteristic has been required in recent years. The inventors of the present invention have made an investigation, and as a result, have found that a triarylamine compound shows a high secondary dispersion characteristic (high $\theta g,F$ characteristic). However, the triarylamine compounds disclosed in Japanese Patent Application Laid-Open No. 2007-011320 and Japanese Patent Application Laid-Open No. 2005-227368 need to be improved before being put into practical use as optical materials (reduced in coloring and improved in transparency). In particular, the improvement of their transmittances has been needed.

In view of such background art, the present invention provides a triarylamine compound having a characteristic in that the dispersion characteristic (Abbe number (vd)) and secondary dispersion characteristic ($\theta g,F$) of refractive indices are high (high $\theta g,F$ characteristic), that is, a chromatic aberration-correction function is high, and having a high transmittance, and a material, an optical element, and an optical apparatus each using the compound.

SUMMARY OF THE INVENTION

According to one aspect of the present invention, there is provided a compound represented by the following general formula (1).

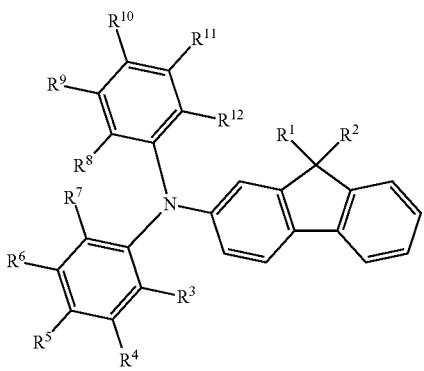

(1)

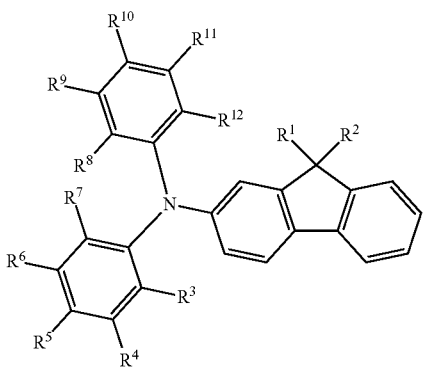

(1)

In the general formula (1), $R^1$ and $R^2$ are each independently selected from a substituted or unsubstituted alkyl group having 1 to 10 carbon atoms, and a substituted or unsubstituted alkylene group having 1 to 8 carbon atoms, the alkylene group having a polymerizable functional group, and $R^3$ to $R^{12}$ are each independently selected from a hydrogen atom, a cyano group, a trifluoromethyl group, a substituted or unsubstituted alkyl group, a substituted or unsubstituted alkylene group having a polymerizable functional group, and a polymerizable functional group, provided that at least one of $R^3$ to $R^{12}$ represents an electron-withdrawing group, and at least one of $R^1$ to $R^{12}$ has a polymerizable functional group.

According to another aspect of the present invention, there is provided a material including a polymerized product (cured product) of the compound.

According to still another aspect of the present invention, there is provided an optical element obtained by molding the material.

According to still yet another aspect of the present invention, there is provided an optical apparatus including the optical element.

Further features of the present invention will become apparent from the following description of exemplary embodiments with reference to the attached drawings.

DESCRIPTION OF THE EMBODIMENTS

The present invention is described in detail below by way of embodiments. In the following description, the term "high θg,F characteristic" means a characteristic included in the range A in FIG. 1.

One aspect of the present invention is a triarylamine compound represented by the following general formula (1).

In the general formula (1), $R^1$ and $R^2$ are each independently selected from a substituted or unsubstituted alkyl group having 1 to 10 carbon atoms, and a substituted or unsubstituted alkylene group having 1 to 8 carbon atoms, the alkylene group having a polymerizable functional group, and $R^3$ to $R^{12}$ are each independently selected from a hydrogen atom, a cyano group, a trifluoromethyl group, a substituted or unsubstituted alkyl group, a substituted or unsubstituted alkylene group having a polymerizable functional group, and a polymerizable functional group, provided that at least one of $R^3$ to $R^{12}$ represents an electron-withdrawing group, and at least one of $R^1$ to $R^{12}$ has a polymerizable functional group.

Figure 1:
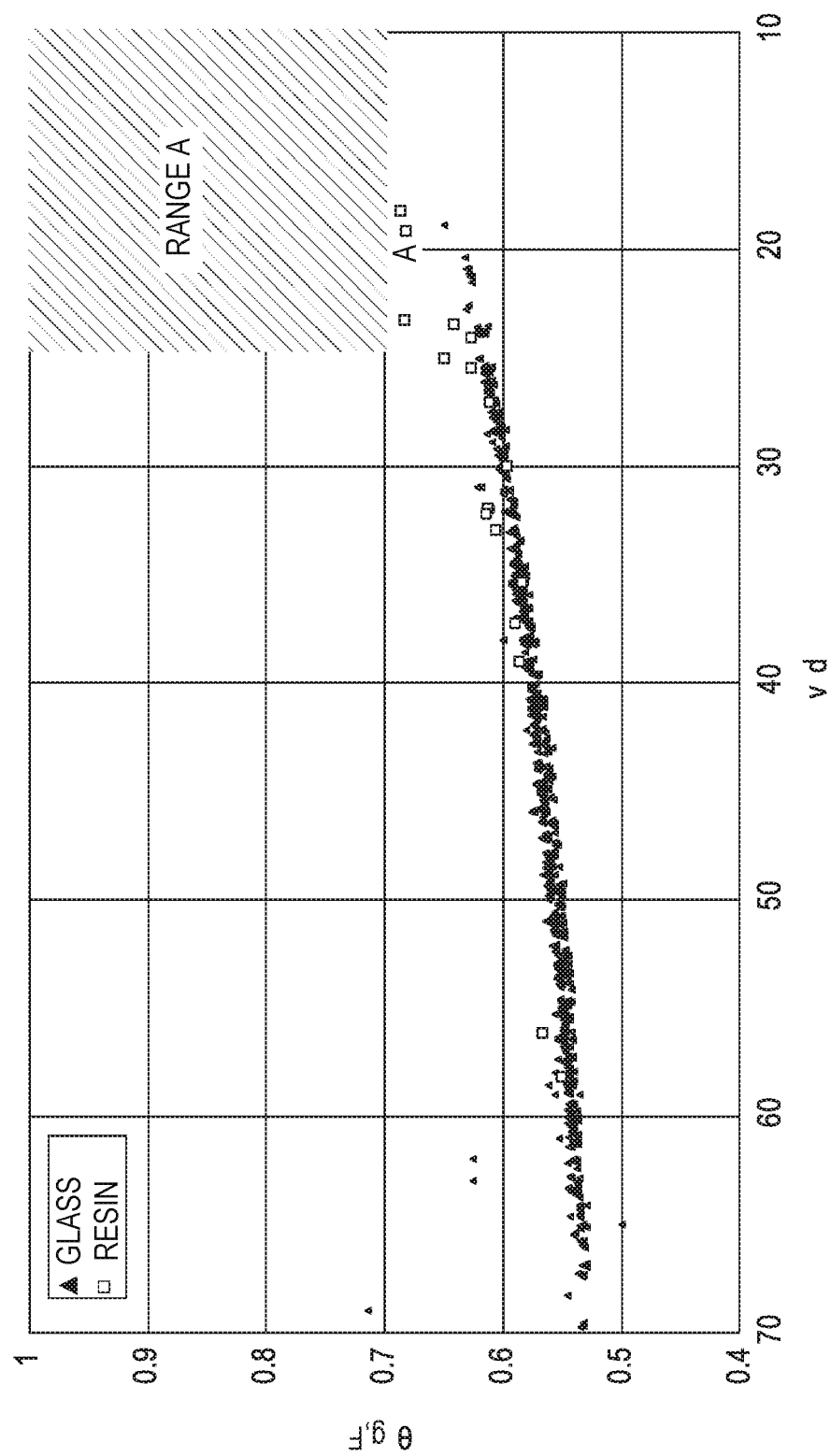
FIG. 1 is a graph for showing a relationship between the secondary dispersion characteristic and Abbe number of a commercially available optical material.

The inventors of the present invention have made extensive investigations with a view to providing a triarylamine compound satisfying a characteristic in the range A in FIG. 1 and having a high transmittance, and as a result, have found that such a structure that the aryl groups of a triarylamine compound are formed of a fluorenyl group and two phenyl groups, and at least one of the phenyl groups has an electron-withdrawing group as a substituent provides a material having both a high secondary dispersion characteristic (high θg,F) and a high transmittance.

In general, a compound having a long conjugated structure typified by an aromatic compound has a band gap smaller than that of a general-purpose material, and hence its absorption edge in a UV region shifts to a visible light region. Under the influence of the shift, the compound having a long conjugated structure has a high refractive index characteristic. The high refractive index characteristic has a larger influence on shorter wavelengths than on longer wavelengths. Accordingly, an improvement in secondary dispersion characteristic (θg,F) of the compound inevitably advances, and hence the characteristic of the compound falls within the range A in FIG. 1. However, a material having practicality is not obtained merely by linking aromatic compounds to build a long conjugated structure. For example, a large aromatic compound involves problems in terms of synthesizability, compatibility with any other compound, and coloring. Meanwhile, a triarylamine is an aromatic compound having an electron-donating property and having a conjugated structure. As its conjugated structure becomes longer, its characteristic (θg,F) is improved. However, when the conjugated structure becomes excessively long, the transmittance of the triarylamine at shorter wavelengths in the visible light region reduces. Accordingly, when the triarylamine is utilized as an optical material, the length of the conjugated structure needs to be adjusted from the viewpoint of an improvement in transmittance. However, an action for improving the transmittance of an aromatic compound, such as the shortening of the conjugated structure of the aromatic compound or the widening of the intermolecular distance thereof by the steric hindrance of a substituent thereof, simultaneously causes a reduction in secondary dispersion characteristic (θg,F) thereof.

The inventors of the present invention have considered the reason why the triarylamine compound according to the present invention has both a high secondary dispersion characteristic (high θg,F) and a high transmittance to be as described below. The substitution of a phenyl group with an electron-withdrawing group is assumed to exhibit an improving effect on the secondary dispersion characteristic (θg,F) by the electron withdrawal of the electron-withdrawing group in addition to an improvement in transmittance by the steric hindrance thereof. The inventors have considered that, as a result of the foregoing, a reduction in secondary dispersion characteristic (θg,F) by the steric hindrance of the electron-withdrawing group is suppressed, and hence the triarylamine compound has both a high secondary dispersion characteristic (high θg,F) and a high transmittance.

In the general formula (1), examples of the substituted or unsubstituted alkyl group having 1 to 10 carbon atoms represented by $R^1$ and $R^2$ include a methyl group, an ethyl group, a n-propyl group, a n-butyl group, a n-pentyl group, a n-hexyl group, a n-heptyl group, a n-octyl group, a n-decyl group, an iso-propyl group, an iso-butyl group, a sec-butyl group, a tert-butyl group, an iso-pentyl group, a neopentyl group, and a 2-ethylhexyl group, and the alkyl group is not limited thereto as long as a high θg,F characteristic is obtained. Of those, an alkyl group having 1 or more to 8 or less carbon atoms is preferred, and a methyl group and an ethyl group are more preferred.

In the general formula (1), examples of the unsubstituted alkylene group having 1 to 8 carbon atoms, which has a polymerizable functional group, represented by $R^1$ and $R^2$ include a methylene group, an ethylene group, a n-propylene group, an iso-propylene group, a n-butylene group, a n-pentylene group, and a n-hexylene group, and the alkylene group is not limited thereto as long as a high θg,F characteristic is obtained. Of those, a methylene group, an ethylene group, a n-propylene group, and a n-butylene group are preferred.

In the general formula (1), examples of the substituted alkylene group having 1 to 8 carbon atoms, which has a polymerizable functional group, represented by $R^1$ and $R^2$ include a group introduced by substituting at least one $CH_2$ in a main chain of an alkylene group with an oxygen atom, and a group introduced by substituting at least one $CH_2$ in a main chain of an alkylene group with a sulfur atom, and the alkylene group is not limited thereto as long as a high θg,F characteristic is obtained.

In the general formula (1), examples of the substituted or unsubstituted alkyl group represented by $R^3$ to $R^{12}$ include a methyl group, an ethyl group, a n-propyl group, a n-butyl group, an iso-propyl group, an iso-butyl group, a sec-butyl group, and a tert-butyl group, and the alkyl group is not limited thereto as long as a high θg,F characteristic is obtained. Of those, a methyl group and an ethyl group are preferred.

In the general formula (1), examples of the unsubstituted alkylene group having a polymerizable functional group represented by $R^3$ to $R^{12}$ include a methylene group, an ethylene group, a n-propylene group, a n-butylene group, a n-pentylene group, and a n-hexylene group, and the alkylene group is not limited thereto as long as a high θg,F characteristic is obtained. Of those, a methylene group, an ethylene group, and a n-propylene group are preferred.

In the general formula (1), examples of the substituted (obtained by substitution) alkylene group having 1 to 8 carbon atoms, which has a polymerizable functional group, represented by $R^3$ to $R^{12}$ include a group introduced by substituting at least one $CH_2$ in a main chain of an alkylene group with an oxygen atom, and a group introduced by substituting at least one $CH_2$ in a main chain of an alkylene group with a sulfur atom, and the alkylene group is not limited thereto as long as a high θg,F characteristic is obtained.

In the general formula (1), examples of the electron-withdrawing substituent include a cyano group, a halogenated alkyl group, a nitro group, an alkylsulfonyl group, an acyl group, an alkoxycarbonyl group, a sulfamoyl group, a carbamoyl group, a halogenated alkoxy group, a sulfonyloxy group, a halogenated alkylthio group, and a fluorine group. Of those, a cyano group and a halogenated alkyl group are preferred, and a cyano group and a trifluoromethyl group are more preferred. It is particularly preferred that at least one of $R^5$, $R^6$, $R^9$, and $R^{10}$ represent an electron-withdrawing group, and the electron-withdrawing group be a cyano group or a trifluoromethyl group.

In the general formula (1), examples of the polymerizable functional group include an active hydrogen group, an unsaturated polymerizable group, and an epoxy group. Examples of the active hydrogen group include a hydroxy group, a carboxyl group, an amino group, a thiol group, and a methoxy group. Of those, a hydroxy group is preferred. Examples of the unsaturated polymerizable group include a vinyl group, an acryloyloxy group, and a methacryloyloxy group. Of those, an acryloyloxy group and a methacryloyloxy group are preferred.

In the present invention, the expression "at least one of $R^3$ to $R^{12}$ has a polymerizable functional group" means that the at least one substituent is a polymerizable functional group, or part of the substituent includes a polymerizable functional group. In other words, in the triarylamine compound according to the present invention, a phenyl group may be directly substituted with a polymerizable functional group, or the polymerizable functional group may be indirectly bonded to the phenyl group through an alkylene group.

In the general formula (1), the number of polymerizable functional groups is preferably 2 or more from the viewpoint of the curability of the triarylamine compound, and is more preferably 2 from the viewpoint of the ease of synthesis thereof.

Next, specific examples of the compound according to the present invention are shown in Tables 1 to 5 below, but the present invention is not limited thereto. In addition, a plurality of compounds may be used in combination. That is, an optical material according to the present invention may be a homopolymer of the compound represented by the general formula (1), or may be a copolymer thereof.

TABLE 1
| No. | Compound Example |
|---|---|
| N1 | |
| N2 | |
| N3 | |
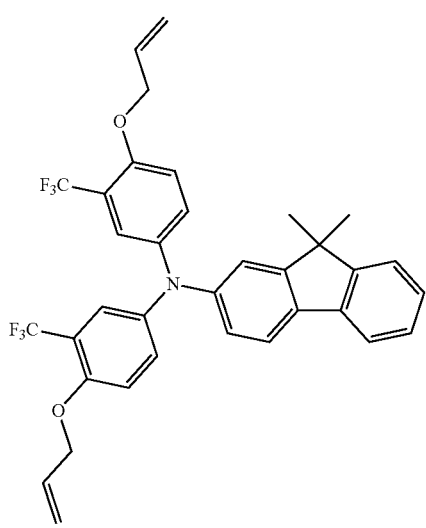 [SMILES: C=CCOc1ccc(N(c2ccc(OCC=C)c(C(F)(F)F)c2)c2ccc3c(c2)C(C)(C)c2ccccc2-3)cc1C(F)(F)F]
TABLE 1-continued
| No. | Compound Example |
|---|---|
| N4 | |
| N5 | |
| N6 | |
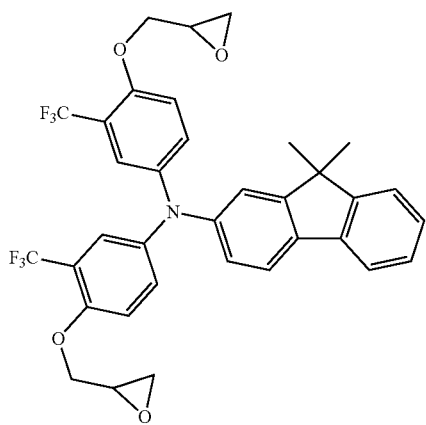 [SMILES: CC1(C)c2ccccc2-c2ccc(N(c3ccc(OCC4CO4)c(C(F)(F)F)c3)c3ccc(OCC4CO4)c(C(F)(F)F)c3)cc21]

TABLE 1-continued

| No. | Compound Example |
|---|---|
| N7 | |
| N8 | |
| N9 | |
| N10 | |

TABLE 2

| No. | Compound Example |
|---|---|
| N11 | |
| N12 | |
| N13 | |

TABLE 2-continued

| No. | Compound Example |
|---|---|
| N14 | (structure) |
| N15 | (structure) |
| N16 | (structure) |
| N17 | (structure) |
| N18 | (structure) |
| N19 | (structure) |

TABLE 2-continued
| No. | Compound Example |
|---|---|
| N20 | 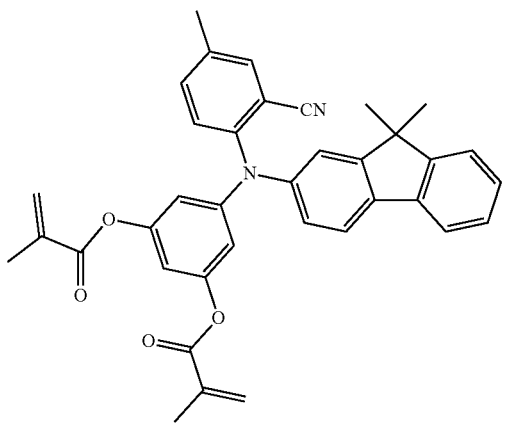 [SMILES: C=C(C)C(=O)Oc1cc(OC(=O)C(=C)C)cc(N(c2ccc3c(c2)C(C)(C)c2ccccc2-3)c2ccc(C)cc2C#N)c1] |
TABLE 3
| No. | Compound Example |
|---|---|
| N21 | |
| N22 | |
TABLE 3-continued
| No. | Compound Example |
|---|---|
| N23 | |
| N24 | |
| N25 | |
| N26 | |

TABLE 3-continued

| No. | Compound Example |
|---|---|
| N27 | |
| N28 | |
| N29 | |
| N30 | |

TABLE 4

| No. | Compound Example |
|---|---|
| N31 | |
| N32 | |
| N33 | |
| N34 | |

TABLE 4-continued

| No. | Compound Example |
|---|---|
| N35 | |
| N36 | |
| N37 | |
| N38 | |

TABLE 4-continued

| No. | Compound Example |
|---|---|
| N39 | |
| N40 | |

TABLE 5

| No. | Compound Example |
|---|---|
| N41 | |

TABLE 5-continued

| No. | Compound Example |
|---|---|
| N42 | |
| N43 | |
| N44 | |
| N45 | |
| N46 | |
| N47 | |

TABLE 5-continued

| No. | Compound Example |
|---|---|
| N48 | |
| N49 | |
| N50 | |

A method of producing the triarylamine compound according to the present invention is described by way of an example.

The method of producing the triarylamine compound is not limited to any specific production route, and any production method may be adopted. A derivative having a structure represented by the general formula (1) in the present invention may be synthesized by using a known synthesis method described in, for example, Japanese Patent Application Laid-Open No. 2000-066425 or Japanese Patent Application Laid-Open No. 2008-165248.

Two methods are available for introducing a polymerizable functional group into the derivative having a structure represented by the general formula (1). A first method is a method involving directly introducing a polymerizable functional group into the derivative having a structure represented by the general formula (1). A second method is a method involving introducing a structure having a polymerizable functional group or a functional group that may be a precursor of the polymerizable functional group into the derivative having a structure represented by the general formula (1). An example of the second method is a method involving introducing a functional group-containing aryl group through the use of a coupling reaction involving using a metal catalyst and a base based on a monoarylamine derivative.

The following methods are available for causing the derivative having a structure represented by the general formula (1) to have an unsaturated hydrocarbon group (e.g., an acrylic group or a methacrylic group). That is, a method involving causing a (meth)acrylate to act on the derivative having a structure represented by the general formula (1), the derivative having a hydroxy group, or a method involving directly introducing a polymerizable functional group into the derivative having a structure represented by the general formula (1) is available.

The coupling reaction based on the metal catalyst may be arbitrarily selected. For example, the Ullmann reaction involving utilizing copper, the Buchwald-Hartwig reaction involving utilizing an amine or the like, the Suzuki coupling involving utilizing boric acid or the like, the Stille coupling involving utilizing an organotin, or the Negishi coupling involving utilizing an organozinc is suitably used as a typical method.

The (meth)acrylation reaction may be arbitrarily selected. For example, a method involving esterifying a hydroxy group with a (meth)acrylic acid halide or (meth)acrylic anhydride, an ester exchange reaction involving using a lower alcohol ester of (meth)acrylic acid, a direct esterification reaction involving subjecting (meth)acrylic acid and the diol to dehydration condensation through the use of a dehydration condensation agent, such as N,N'-dicyclohexylcarbodiimide, or a method involving heating (meth)acrylic acid and the diol in the presence of a dehydrating agent, such as sulfuric acid, is suitably used as a typical method.

In addition, a polymerization inhibitor may be used as required so that the polymerization of the triarylamine compound of the present invention may not advance at the time of a reaction for the production of the compound or at the time of its storage. Examples of the polymerization inhibitor may include: hydroquinones, such as p-benzoquinone, hydroquinone, hydroquinone monomethyl ether, and 2,5-diphenyl-p-benzoquinone; N-oxy radicals, such as tetramethylpiperidinyl-N-oxy radical (TEMPO); substituted catechols, such as t-butylcatechol; amines, such as phenothiazine, diphenylamine, and phenyl-β-naphthylamine; nitrosobenzene; picric acid; molecular oxygen; sulfur; and copper(II) chloride. Of those, hydroquinones, phenothiazine, and N-oxyradicals are preferred from the viewpoints of a general-purpose property and the suppression of the polymerization, and hydroquinones are particularly preferred.

A lower limit for the usage amount of the polymerization inhibitor is typically 10 ppm or more, preferably 50 ppm or more with respect to the triarylamine compound, and an upper limit therefor is typically 10,000 ppm or less, preferably 1,000 ppm or less with respect thereto. In the case where the usage amount is excessively small, the following risk arises: the effect of the polymerization inhibitor is not expressed or the effect is small even when the effect is expressed, and hence the polymerization advances at the time of the reaction or at the time of condensation in a posttreatment step. In contrast, the case where the usage amount is excessively large is not preferred because the following risk arises: the polymerization inhibitor serves as, for example, an impurity at the time of the production of an optical material to be described later, and has an adverse effect, such as the inhibition of the polymerization reactivity of the triarylamine compound.

Next, the optical material according to the present invention is described.

The optical material according to the present invention is formed of a composition including the above-mentioned triarylamine compound, a polymerization initiator, and the polymerization inhibitor, and as required, a photosensitizer, a heat-resistive stabilizer, a light-resistive stabilizer, an antioxidant, or a resin.

The content of the triarylamine compound to be incorporated into the optical material of the present invention is desirably 1.0 wt % or more to 99 wt % or less, preferably 50 wt % or more to 99 wt % or less with respect to the entirety of the material.

Examples of the polymerization initiator include, but not limited to, a polymerization initiator that generates a radical species or a cation species through light irradiation, and a polymerization initiator that generates a radical species with heat.

Examples of the polymerization initiator that generates a radical species through light irradiation include, but not limited to, 2-benzyl-2-dimethylamino-1-(4-morpholinophenyl)-1-butanone, 1-hydroxycyclohexyl phenyl ketone, 2-hydroxy-2-methyl-1-phenyl-propan-1-one, bis(2,4,6-trimethylbenzoyl)-phenylphosphine oxide, 4-phenylbenzophenone, 4-phenoxybenzophenone, 4,4'-diphenylbenzophenone, and 4,4'-diphenoxybenzophenone.

In addition, suitable examples of the polymerization initiator that generates a cation species through light irradiation include, but not limited to, polymerization initiators such as iodonium (4-methylphenyl)[4-(2-methylpropyl)phenyl]-hexafluorophosphate.

Further, examples of the polymerization initiator that generates a radical species with heat include, but not limited to: azo compounds, such as azobisisobutyronitrile (AIBN); and peroxides, such as benzoyl peroxide, t-butyl peroxypivalate, t-butyl peroxyneohexanoate, t-hexyl peroxyneohexanoate, t-butyl peroxyneodecanoate, t-hexyl peroxyneodecanoate, cumyl peroxyneohexanoate, and cumyl peroxyneodecanoate.

When UV light or the like is applied as light to initiate the polymerization of the optical material, a known sensitizer or the like may be used. Typical examples of the sensitizer include, but not limited to, benzophenone, 4,4-diethylaminobenzophenone, 1-hydroxycyclohexyl phenyl ketone, isoamyl p-dimethylaminobenzoate, methyl 4-dimethylaminobenzoate, benzoin, benzoin ethyl ether, benzoin isobutyl ether, benzoin isopropyl ether, 2,2-diethoxyacetophenone, methyl o-benzoylbenzoate, 2-hydroxy-2-methyl-1-phenyl-propan-1-one, and acylphosphine oxides.

The addition ratio of the photopolymerization initiator with respect to a polymerizable resin component may be appropriately selected in accordance with a light irradiation amount and an additional heating temperature. In addition, the addition ratio may be adjusted in accordance with the target average molecular weight of a polymer to be obtained.

The addition amount of the photopolymerization initiator to be used in the polymerization (curing) and molding of the optical material according to the present invention preferably falls within the range of from 0.01 wt % or more to 10.00 wt % or less with respect to the polymerizable resin component. The photopolymerization initiators may be used alone or in combination thereof in accordance with the reactivity of the resin and the wavelength of the light to be applied.

The light-resistive stabilizer is not particularly limited as long as the light-resistive stabilizer does not have a large influence on the optical characteristics of the molded body, and typical examples thereof may include: benzotriazole-based materials, such as 2-(2H-benzotriazol-2-yl)-p-cresol, 2-(2H-benzotriazol-2-yl)-4,6-bis(1-methyl-1-phenylethyl) phenol, 2-[5-chloro(2H)-benzotriazol-2-yl-4-methyl-6-(tert-butyl)]phenol, 2-(2H-benzotriazol-2-yl)-4,6-di-tert-pentyl-phenol, 2-(2H-benzotriazol-2-yl)-4-(1,1,3,3-tetramethyl-butyl)phenol, 2,2'-methylenebis[6-(2H-benzotriazol-2-yl)-4-(1,1,3,3-tetramethylbutyl)]phenol, and 2-(2H-benzotriazol-2-yl)-6-dodecyl-4-methylphenol; cyanoacrylate-based materials, such as ethyl 2-cyano-3,3-diphenylacrylate and 2-ethylhexyl 2-cyano-3,3-diphenylacrylate; triazine-based materials; and benzophenone-based materials, such as octabenzone and 2,2'-4,4'-tetrahydrobenzophenone. The light-resistive stabilizer may also serve as the photosensitizer, and in that case, the photosensitizer may not be added.

The addition amount of the light-resistive stabilizer to be used in the polymerization (curing) and molding of the optical material of the present invention preferably falls within the range of from 0.01 wt % or more to 10.00 wt % or less with respect to the total amount of the polymerizable resin component.

The heat-resistive stabilizer is not particularly limited as long as the heat-resistive stabilizer does not have a large influence on the optical characteristics of the molded body, and for example: pentaerythritol tetrakis[3-(3,5-di-ert-butyl-4-hydroxyphenyl)]propionate, octadecyl-3-(3,5-di-tert-butyl-4-hydroxyphenyl)propionate, 3,5-bis(1,1-dimethylethyl)-4-hydroxybenzenepropanoic acid, and C7-C9 side chain alkyl esters; hindered phenol-based materials, such as 4,6-bis(octylthiomethyl)-o-cresol, 4,6-bis(dodecylthiomethyl)-o-cresol, ethylenebis(oxyethylene)bis[3-(5-tert-butyl-4-hydroxy-m-tolyl)]propionate, and hexamethylenebis[3-(3,5-di-tert-butyl-4-hydroxyphenyl)]propionate; phosphorus-based materials, such as tris(2,4-di-tert-butylphenyl) phosphite; and sulfur-based materials, such as dioctadecyl 3,3'-thiodipropionate, may be used.

The antioxidant is not particularly limited as long as the antioxidant does not have a large influence on the optical characteristics of the molded body, and typical examples thereof include hindered amine-based materials, such as bis(2,2,6,6-tetramethyl-4-piperidyl) sebacate and bis(1,2,2,6,6-pentamethyl-4-piperidyl)[[3,5-bis(1,1-dimethylethyl)-4-hydroxyphenyl]methyl]butyl malonate. The addition amount of the antioxidant to be used in the polymerization (curing) and molding of the optical material according to the present invention preferably falls within the range of from 0.01 wt % or more to 10.00 wt % or less with respect to the total amount of the polymerizable resin component.

The resin that may be utilized in the optical material of the present invention is not particularly limited. Examples thereof include, but not limited to: (meth)acrylate compounds, such as 1,3-adamantanediol dimethacrylate, 1,3-adamantanedimethanol dimethacrylate, tricyclodecanedimethanol diacrylate, pentaerythritol tetraacrylate, propoxylated neopentyl glycol diacrylate, dipropylene glycol diacrylate, ethoxylated bisphenol A dimethacrylate, tris (2-hydroxyethyl) isocyanurate triacrylate, 2-(2-ethoxyethoxy)ethyl acrylate, stearyl acrylate, tetrahydrofurfuryl acrylate, 2-phenoxyethyl acrylate, isodecyl acrylate, isobornyl acrylate, isobornyl methacrylate, 1,3-butylene glycol diacrylate, 1,4-butanediol diacrylate, diethylene glycol diacrylate, 1,6-hexanediol diacrylate, triethylene glycol diacrylate, tripropylene glycol diacrylate, dipropylene glycol diacrylate, triethylene glycol dimethacrylate, ethylene glycol dimethacrylate, tetraethylene glycol dimethacrylate, 1,4-butanediol dimethacrylate, diethylene glycol dimethacrylate, 1,6-hexanediol dimethacrylate, tripropylene glycol dimethacrylate, dipropylene glycol dimethacrylate, trimethylol propane trimethacrylate, 9,9-bis[4-(2-acryloyloxyethoxy)phenyl]fluorene, 9,9-bis[4-(2-methacryloyloxyethoxy)phenyl]fluorene, 9,9-bis[4-(2-acryloyloxy)phenyl]fluorene, 9,9-bis[4-(2-methacryloyloxy)phenyl]fluorene, benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, 1,1-bis(4-acryloxyethoxyphenyl)sulfone, 1,1-bis(4-methacryloxyethoxyphenyl)sulfone, 1,1-bis(4-acryloxydiethoxyphenyl)sulfone, 1,1-bis(4-methacryloxydiethoxyphenyl)sulfone, dimethyloltricyclodecane diacrylate, trimethylol propane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methyl thioacrylate, methyl thiomethacrylate, phenyl thioacrylate, benzyl thiomethacrylate, xylylene dithiol diacrylate, xylylene dithiol dimethacrylate, mercaptoethyl sulfide diacrylate, and mercaptoethyl sulfide dimethacrylate; allyl compounds, such as allyl glycidyl ether, diallyl phthalate, diallyl terephthalate, diallyl isophthalate, diallyl carbonate, and diethylene glycol bisallyl carbonate; vinyl compounds, such as styrene, chlorostyrene, methylstyrene, bromostyrene, dibromostyrene, divinylbenzene, and 3,9-divinylspirobi(m-dioxane); and diisopropenylbenzene.

In addition, the resin may be a thermoplastic resin. Examples thereof include: polyolefin-based resins, such as an ethylene homopolymer, a random or block copolymer of ethylene and one or two or more kinds of α-olefins, such as propylene, 1-butene, 1-pentene, 1-hexene, and 4-methyl-1-pentene, a random or block copolymer of ethylene and one or two or more kinds of vinyl acetate, acrylic acid, methacrylic acid, methyl acrylate, and methyl methacrylate, a propylene homopolymer, a random or block copolymer of propylene and one or two or more kinds of α-olefins except propylene, such as 1-butene, 1-pentene, 1-hexene, and 4-methyl-1-pentene, a 1-butene homopolymer, an ionomer resin, and a mixture of those polymers; hydrocarbon atom-based resins, such as a petroleum resin and a terpene resin; polyester-based resins, such as polyethylene terephthalate, polybutylene terephthalate, and polyethylene naphthalate; polyamide-based resins, such as nylon 6, nylon 66, nylon 11, nylon 12, nylon 610, nylon 6/66, nylon 66/610, and nylon MXD; acrylic resins, such as polymethyl methacrylate; styrene- or acrylonitrile-based resins, such as polystyrene, a styrene-acrylonitrile copolymer, a styrene-acrylonitrile-butadiene copolymer, and polyacrylonitrile; polyvinyl alcohol-based resins, such as polyvinyl alcohol and an ethylene-vinyl alcohol copolymer; polycarbonate resins; polyketone resins; polymethylene oxide resins; polysulfone resins; polyimide resins; and polyamide imide resins. Those resins may be used alone or as a mixture thereof.

The content of the resin to be incorporated into the optical material according to the present invention is desirably 0.01 wt % or more to 99 wt % or less, and is preferably 0.01 wt % or more to 50 wt % or less in consideration of the $\theta g, F$ characteristic of the optical material to be obtained and the brittleness of the molded body.

Next, an optical element according to the present invention is described with reference to the drawings.

Figure 2A:
FIG. 2A is a schematic view for illustrating an example of an optical element according to the present invention.
Figure 2B:
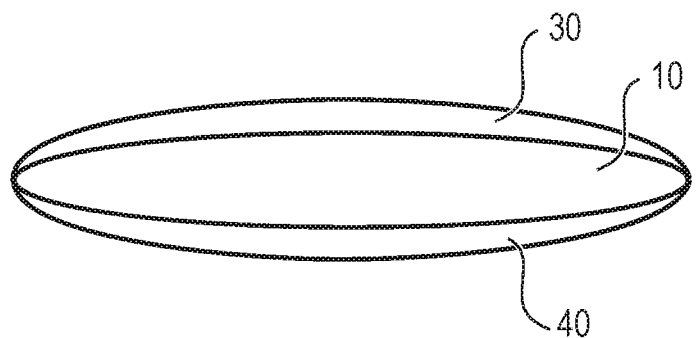
FIG. 2B is a schematic view for illustrating an example of the optical element according to the present invention.

The optical element of the present invention has a feature of including the molded body. FIG. 2A and FIG. 2B are each a schematic view for illustrating an example of the optical element of the present invention. In an optical element of FIG. 2A, a thin film (optical member 10) obtained by molding and processing the optical material (or the optical composition) is arranged on one surface of a lens substrate 20. As a method of producing the optical element of FIG. 2A, for example, a method involving forming a layer structure having a small thickness on a substrate formed of a light-transmitting material is adopted. Specifically, a die formed of a metal material is arranged so as to have a certain distance from a glass substrate, and a gap present between the die and the glass substrate is filled with the optical material or the optical composition that is fluid. After that, die molding is performed by lightly pressing down the die. Then, the optical material or the optical composition is polymerized while being kept in the state as required.

Light irradiation to be used in such polymerization reaction is performed by using light having a suitable wavelength, typically UV light or visible light in correspondence with a mechanism resulting from radical formation involving using a photopolymerization initiator. For example, raw materials, such as the monomers of the optical material or the optical composition subjected to the die molding, are uniformly irradiated with the light through the light-transmitting material to be utilized as the substrate, specifically the glass substrate. An irradiation light amount is appropriately selected in accordance with the mechanism resulting from the radical formation involving utilizing the photopolymerization initiator and with the content of the photopolymerization initiator to be incorporated.

Meanwhile, in such production of the molded body of the optical material or the optical composition by a photopolymerization reaction, it is more preferred that the entirety of the raw materials, such as the monomers, subjected to the die molding be uniformly irradiated with the irradiation light. Therefore, it is more preferred to select light having such a wavelength that the light irradiation to be utilized can be uniformly performed through the light-transmitting material to be utilized as the substrate, such as the glass substrate. At this time, a reduction in thickness of the molded body of the optical material to be formed on the substrate of the light-transmitting material is more suitable for the present invention.

Meanwhile, in an optical element of FIG. 2B, the thin film (optical member 10) obtained by molding and processing the optical composition is arranged between a lens substrate 30 and a lens substrate 40. A method of producing the optical element of FIG. 2B is, for example, as described below. A similar uncured optical material, optical composition, or the like is poured into a gap between both the surface of the optical material or optical composition of the molded body described in the foregoing and another corresponding lens, and is molded by being lightly pressed down. Then, the photopolymerization of the uncured resin composition is performed while the composition is kept in the state. Thus, a molded body in which the optical material or the optical composition is sandwiched between the lenses can be obtained.

Similarly, the molded body may be produced by a thermal polymerization method. In this case, it is desired that the temperature of the entirety of the composition be further uniformized, and a reduction in total thickness of the molded body of the polymerizable composition to be formed on the substrate of the light-transmitting material is more suitable for the present invention. In addition, when the total thickness of the molded body of the optical composition to be formed is increased, an irradiation amount, an irradiation intensity, a light source, and the like need to be selected while the thickness, the absorption of a resin component, and the absorption of a fine particle component are further considered.

The molded body obtained by molding the optical composition of the present invention in accordance with the above-mentioned molding method may be used as an optical element in an optical apparatus. The optical element is utilized in, for example, a camera lens.

EXAMPLES

The present invention is described in more detail below by way of Examples. However, the present invention is by no means limited by Examples described below as long as the other examples do not depart from the gist of the present invention. A synthesized product was analyzed with a NMR apparatus (JNM-ECA400 (trade name) manufactured by JEOL Ltd.).

Example 1

(Production of Compound Example N1)
(1) Synthesis of N1 Intermediate

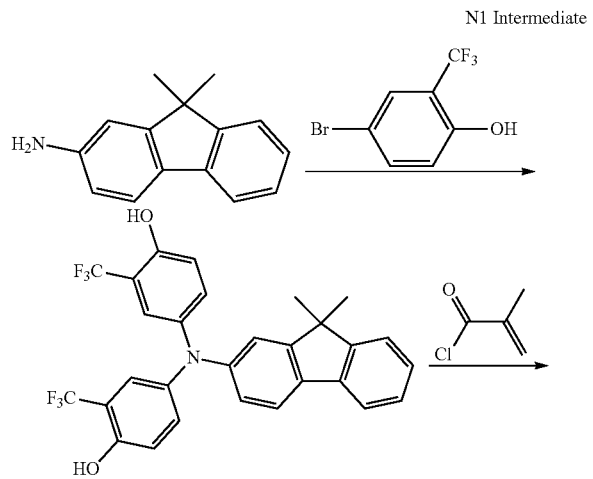

N1 Intermediate

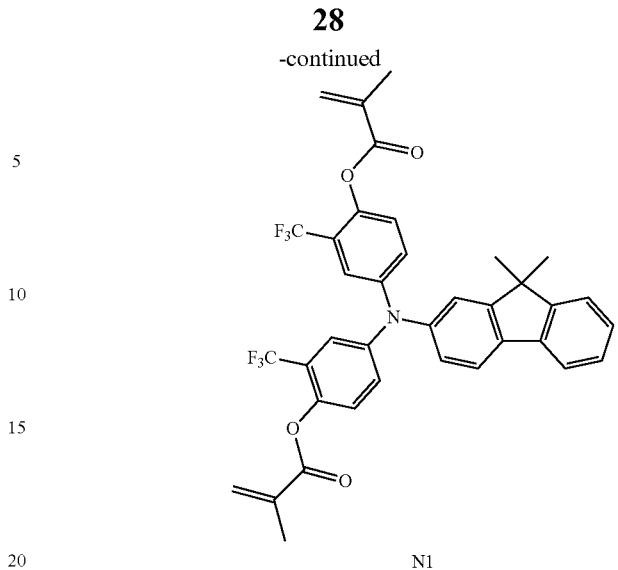

N1

Under a nitrogen atmosphere, 2.0 g of 2-amino-9,9-dimethylfluorene, 5.30 g of 4-bromo-2-(trifluoromethyl) phenol, 2.76 g of sodium tert-butoxide, 0.27 g of bis(dibenzylideneacetone)palladium, 0.46 g of 2-dicyclohexylphosphino-2',4',6'-triisopropylbiphenyl, and 70 mL of orthoxylene were loaded into a 200-milliliter three-necked flask, and the mixture was heated to 130° C. After that, the mixture was stirred at the temperature (130° C.) for 10 hours. After the heating, the mixture was left to cool to room temperature, and then the organic phase was extracted with chloroform. The resultant organic phase was washed with brine and water in the stated order, and was dried with anhydrous magnesium sulfate. The resultant crude product was purified by column chromatography to provide 2.2 g of an N1 intermediate (yield: 43%). The structure of the intermediate was identified by $^1$H-NMR.

$^1$H-NMR (CDCl$_3$): δ 1.52 (s, 6H), 6.96 (d, 1H), 7.31-7.37 (m, 3H), 7.44 (d, 1H), 7.50-7.55 (m, 2H), 7.67 (d, 1H), 7.70-7.75 (m, 4H), 7.93 (s, 1H), 11.96 (s, 2H)

(2) Synthesis of N1

Under a nitrogen atmosphere, 2.0 g of the N1 intermediate, 30 mL of chloroform, 0.14 g of hydroquinone monomethyl ether (MEHQ), and 10 mL of pyridine were loaded into a 100-milliliter three-necked flask. The reaction vessel was cooled to 0° C., and 1.0 mL of methacryloyl chloride was dropped into the mixture. The reaction liquid was diluted with 30 mL of toluene, and then a 2 N aqueous solution of hydrochloric acid was used to terminate the reaction. The resultant organic layer was washed with an acidic aqueous solution and a basic aqueous solution. After that, the organic layer was dried with brine and anhydrous magnesium sulfate. The solvent was removed, and the resultant crude product was purified by silica gel chromatography. Thus, 1.25 g of the N1 was obtained (yield: 50%). The structure of the product was identified by $^1$H-NMR. In addition, the optical characteristics of the product are shown in Table 6.

$^1$H-NMIR (CDCl$_3$): δ 1.49 (s, 6H), 1.54 (s, 6H), 5.88 (t, 2H), 6.46 (t, 2H), 7.10 (d, 1H), 7.28-7.43 (m, 5H), 7.63-7.71 (m, 4H), 7.78 (d, 1H), 8.10 (d, 1H), 8.17 (d, 1H)

Example 2

(Production of Compound Example N22)
(1) Synthesis of N22 Intermediate 1

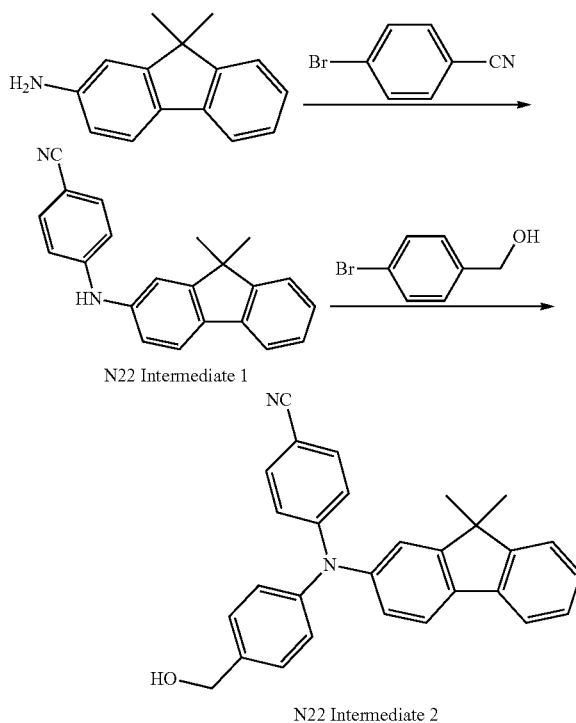

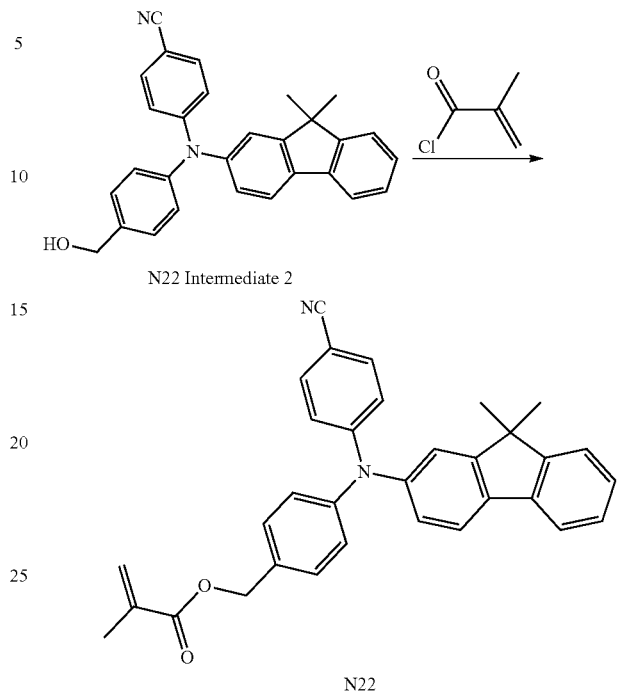

Under a nitrogen atmosphere, 5.0 g of 2-amino-9,9-dimethylfluorene, 4.35 g of 4-bromobenzonitrile, 6.89 g of sodium tert-butoxide, 0.27 g of bis(dibenzylideneacetone) palladium, 0.46 g of 2-dicyclohexylphosphino-2,'4',6'-triisopropylbiphenyl, and 180 mL of orthoxylene were loaded into a 300-milliliter three-necked flask, and the mixture was heated to 130° C. After that, the mixture was stirred at the temperature (130° C.) for 10 hours. After the heating, the mixture was left to cool to room temperature, and then the organic phase was extracted with chloroform. The resultant organic phase was washed with brine and water in the stated order, and was dried with anhydrous magnesium sulfate. The resultant crude product was purified by column chromatography to provide 7.5 g of an N22 intermediate 1 (yield: 72%).

(2) Synthesis of N22 Intermediate 2

Under a nitrogen atmosphere, 4.0 g of the N22 intermediate 1, 3.37 g of 4-bromobenzyl alcohol, 4.95 g of sodium tert-butoxide, 0.37 g of bis(dibenzylideneacetone)palladium, 0.61 g of 2-dicyclohexylphosphino-2,'4',6'-triisopropylbiphenyl, and 140 mL of orthoxylene were loaded into a 200-milliliter three-necked flask, and the mixture was heated to 130° C. After that, the mixture was stirred at the temperature (130° C.) for 10 hours. After the heating, the mixture was left to cool to room temperature, and then the organic phase was extracted with chloroform. The resultant organic phase was washed with brine and water in the stated order, and was dried with anhydrous magnesium sulfate. The resultant crude product was purified by column chromatography to provide 3.4 g of an N22 intermediate 2 (yield: 63%).

(3) Synthesis of N22

Under a nitrogen atmosphere, 3.0 g of the N22 intermediate 2, 45 mL of chloroform, 0.27 g of MEHQ, and 10 mL of pyridine were loaded into a 100-milliliter three-necked flask. The reaction vessel was cooled to 0° C., and 2.1 mL of methacryloyl chloride was dropped into the mixture. The reaction liquid was diluted with 30 mL of toluene, and then a 2 N aqueous solution of hydrochloric acid was used to terminate the reaction. The resultant organic layer was washed with an acidic aqueous solution and a basic aqueous solution. After that, the organic layer was dried with brine and anhydrous magnesium sulfate. The solvent was removed, and the resultant crude product was purified by silica gel chromatography. Thus, 1.51 g of the N22 was obtained (43%). The structure of the product was identified by $^1$H-NMR. In addition, the optical characteristics of the product are shown in Table 6.

$^1$H-NMR (CDCl$_3$): δ δ 1.49 (s, 6H), 1.53 (s, 6H), 5.05-5.11 (m, 2H), 5.50 (t, 1H), 6.02 (t, 1H), 6.85 (dd, 1H), 7.05 (dd, 1H), 7.19 (d, 4H), 7.30-7.36 (m, 2H), 7.40 (d, 1H), 7.48 (d, 4H), 7.63 (d, 2H)

Example 3

(Production of Compound Example N31)
(1) Synthesis of N31 Intermediate 1

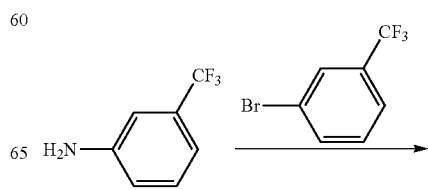

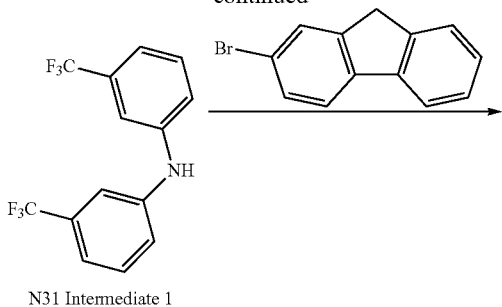

N31 Intermediate 1

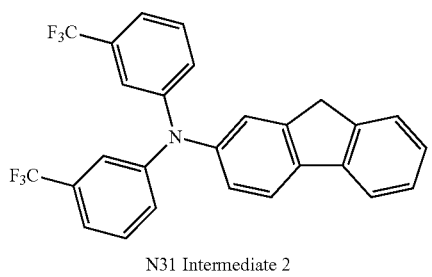

N31 Intermediate 2

Under a nitrogen atmosphere, 15.0 g of 3-aminobenzotrifluoride, 20.95 g of 3-bromobenzotrifluoride, 26.85 g of sodium tert-butoxide, 2.68 g of bis(dibenzylideneacetone) palladium, 4.44 g of 2-dicyclohexylphosphino-2,'4',6'-triisopropylbiphenyl, and 300 mL of orthoxylene were loaded into a 500-milliliter three-necked flask, and the mixture was heated to 120° C. After that, the mixture was stirred at the temperature (120° C.) for 6 hours. After the heating, the mixture was left to cool to room temperature, and then the organic phase was extracted with ethyl acetate. The resultant organic phase was washed with brine and water in the stated order, and was dried with anhydrous magnesium sulfate. The resultant crude product was purified by column chromatography to provide 19.2 g of an N31 intermediate 1 (yield: 68%).

(2) Synthesis of N31 Intermediate 2

Under a nitrogen atmosphere, 15.0 g of the N31 intermediate 1, 12.05 g of 2-bromofluorene, 18.89 g of sodium tert-butoxide, 0.28 g of bis(dibenzylideneacetone)palladium, 0.47 g of 2-dicyclohexylphosphino-2,'4',6'-triisopropylbiphenyl, and 500 mL of orthoxylene were loaded into a 1-liter three-necked flask, and the mixture was heated to 120° C. After that, the mixture was stirred at the temperature (120° C.) for 10 hours. After the heating, the mixture was left to cool to room temperature, and then the organic phase was extracted with ethyl acetate. The resultant organic phase was washed with brine and water in the stated order, and was dried with anhydrous magnesium sulfate. The resultant crude product was purified by column chromatography to provide 10.5 g of an N31 intermediate 2 (yield: 46%).

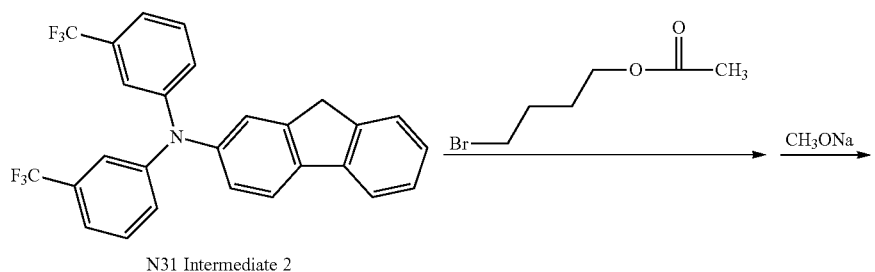

N31 Intermediate 2

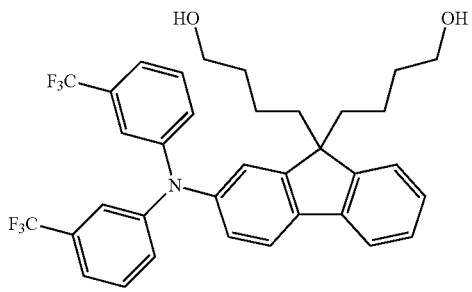

N31 Intermediate 3

(3) Synthesis of N31 Intermediate 3

Under a nitrogen atmosphere, 9.44 g of the N31 intermediate 2 and 160 mL of N,N-dimethylacetamide were loaded into a 500-milliliter three-necked flask, and the mixture was stirred. After that, 6.77 g of sodium tert-butoxide was loaded into the mixture, and the whole was cooled to 5° C. A solution obtained by dissolving 10.21 g of 4-bromobutyl acetate in 40 mL of N,N-dimethylacetamide was dropped into the resultant over 30 minutes. After the dropping, the temperature of the mixture was increased to 20° C., and then the mixture was stirred at the temperature (20° C.) for 20 hours. After the stirring, the mixture was cooled to 5° C. Next, 5.44 g of sodium methoxide was loaded into the mixture, and the temperature of the whole was gradually increased to 20° C. After the temperature increase, the mixture was stirred at the temperature (20° C.) for 10 hours. After the stirring, the reaction liquid was loaded into ice water, and the organic layer was extracted with toluene. The resultant organic phase was washed with brine and water in the stated order, and was dried with anhydrous magnesium sulfate. The resultant crude product was purified by column chromatography to provide 5.5 g of an N31 intermediate 3 (yield: 45%). The structure of the product was identified by $^1$H-NMR.

$^1$H-NMR (CDCl$_3$): δ 0.71 (t, 2H), 1.38 (d, 4H), 1.60 (d, 4H), 1.94-2.00 (m, 4H), 3.22-3.29 (m, 4H), 7.08 (dd, 1H), 7.17 (d, 1H), 7.26-7.43 (m, 11H), 7.67 (t, 2H)

3) Synthesis of N31

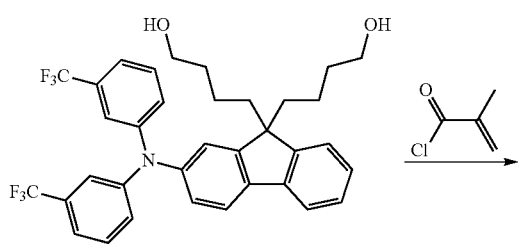

N31 Intermediate 3

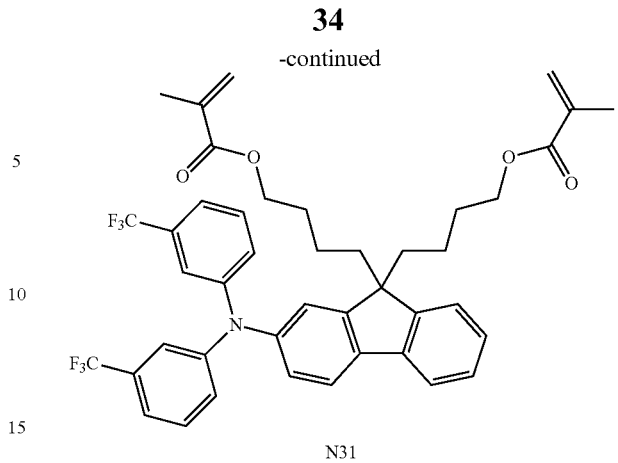

N31

Under a nitrogen atmosphere, 5.0 g of the N31 intermediate 3, 175 mL of tetrahydrofuran, 0.30 g of MEHQ, and 4.6 mL of triethylamine were loaded into a 300-milliliter three-necked flask. The reaction vessel was cooled to 0° C., and 2.3 mL of methacryloyl chloride was dropped into the mixture. The reaction liquid was diluted with toluene, and then a 2 N aqueous solution of hydrochloric acid was used to terminate the reaction. The resultant organic layer was washed with an acidic aqueous solution and a basic aqueous solution. After that, the organic layer was dried with brine and anhydrous magnesium sulfate. The solvent was removed, and the resultant crude product was purified by silica gel chromatography. Thus, 1.65 g of the N31 was obtained (27%). The structure of the product was identified by $^1$H-NMR. In addition, the optical characteristics of the product are shown in Table 6.

$^1$H-NMR (CDCl$_3$): δ 1.42 (d, 4H), 1.71 (d, 4H), 1.78 (s, 6H), 2.13-2.18 (m, 4H), 3.22-3.27 (m, 4H), 5.43 (t, 2H), 5.80 (t, 2H), 6.90 (dd, 1H), 7.10 (dd, 1H), 7.22 (d, 4H), 7.30-7.36 (m, 2H), 7.42 (d, 1H), 7.50 (d, 4H), 7.65 (d, 2H)

Example 4

(Production of Compound Example N32)
(1) Synthesis of N32 Intermediate 1

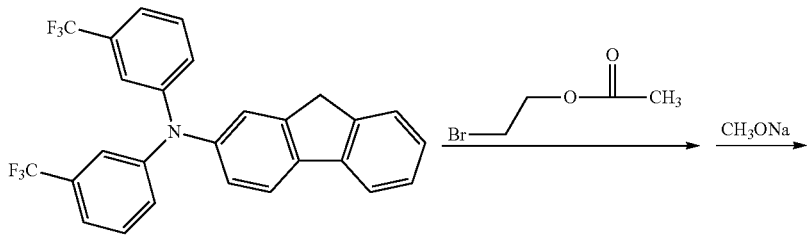

N31 Intermediate 2

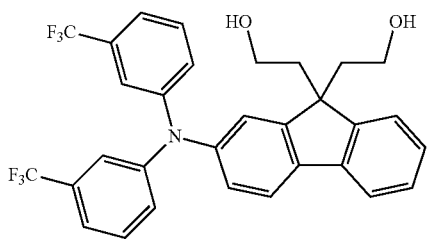

N32 Intermediate 1

Under a nitrogen atmosphere, 10.00 g of the N31 intermediate 2 and 80 mL of N,N-dimethylacetamide were loaded into a 300-milliliter three-necked flask, and the mixture was stirred. After that, 7.17 g of sodium tert-butoxide was loaded into the mixture, and the whole was cooled to 5° C. A liquid obtained by dissolving 9.25 g of 2-bromoethyl acetate in 20 mL of N,N-dimethylacetamide was dropped into the resultant over 30 minutes. After the dropping, the temperature of the mixture was increased to 20° C., and then the mixture was stirred at the temperature (20° C.) for 20 hours. After the stirring, the mixture was cooled to 5° C. 5.75 g of sodium methoxide was loaded into the mixture, and the temperature of the whole was gradually increased to 20° C. After the temperature increase, the mixture was stirred at the temperature (20° C.) for 10 hours. After the stirring, the reaction liquid was loaded into ice water, and the organic layer was extracted with toluene. The resultant organic phase was washed with brine and water in the stated order, and was dried with anhydrous magnesium sulfate. The resultant crude product was purified by column chromatography to provide 4.2 g of an N32 intermediate 1 (yield: 35%). The structure of the product was identified by $^1$H-NMR.

$^1$H-NMR (CDCl$_3$): δ 0.71 (t, 2H), 2.21-2.27 (m, 2H), 2.31-2.37 (m, 2H), 3.02-3.12 (m, 4H), 7.08 (dd, 1H), 7.18 (d, 1H), 7.27-7.44 (m, 11H), 7.67 (t, 2H)

(2) Synthesis of N32

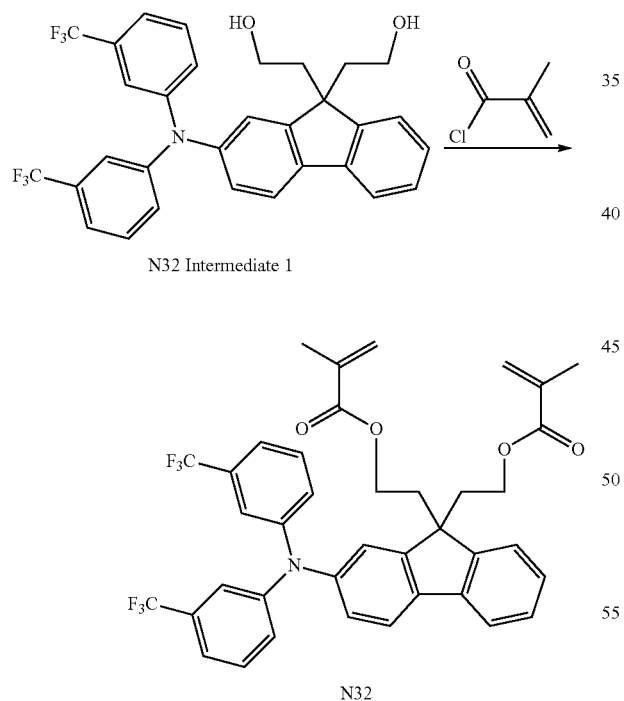

N32 Intermediate 1

N32

Under a nitrogen atmosphere, 3.0 g of the N32 intermediate 1, 105 mL of tetrahydrofuran, 0.20 g of MEHQ, and 3.0 mL of triethylamine were loaded into a 300-milliliter three-necked flask. The reaction vessel was cooled to 0° C., and 1.5 mL of methacryloyl chloride was dropped into the mixture. The reaction liquid was diluted with toluene, and then a 2 N aqueous solution of hydrochloric acid was used to terminate the reaction. The resultant organic layer was washed with an acidic aqueous solution and a basic aqueous solution. After that, the organic layer was dried with brine and anhydrous magnesium sulfate. The solvent was removed, and the resultant crude product was purified by silica gel chromatography. Thus, 1.91 g of the N32 was obtained (52%). The structure of the product was identified by $^1$H-NMR. In addition, the optical characteristics of the product are shown in Table 6.

$^1$H-NMR (CDCl$_3$): δ 1.78 (s, 6H), 2.29-2.34 (m, 2H), 2.42-2.47 (m, 2H), 3.45-3.50 (m, 2H), 3.61-3.66 (m, 2H), 5.43 (t, 2H), 5.81 (t, 2H), 6.90 (dd, 1H), 7.10 (dd, 1H), 7.21 (d, 4H), 7.30-7.36 (m, 2H), 7.42 (d, 1H), 7.51 (d, 4H), 7.65 (d, 2H)

Example 5

(Production of Compound Example N33)
(1) Synthesis of N33 Intermediate 1

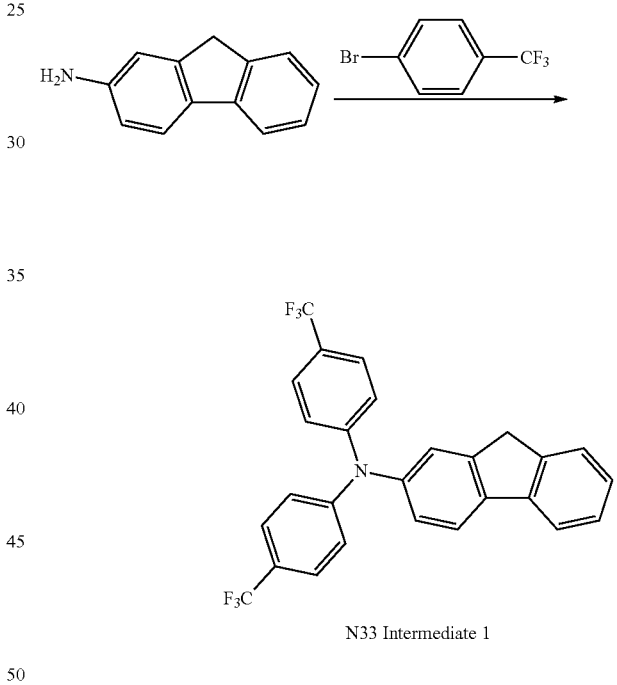

N33 Intermediate 1

Under a nitrogen atmosphere, 5.0 g of 2-aminofluorene, 12.72 g of 4-bromobenzotrifluoride, 10.61 g of sodium tert-butoxide, 0.16 g of bis(dibenzylideneacetone)palladium, 0.26 g of 2-dicyclohexylphosphino-2,'4',6'-triisopropylbiphenyl, and 175 mL of orthoxylene were loaded into a 500-milliliter three-necked flask, and the mixture was heated to 120° C. After that, the mixture was stirred at the temperature (120° C.) for 6 hours. After the heating, the mixture was left to cool to room temperature, and then the organic phase was extracted with ethyl acetate. The resultant organic phase was washed with brine and water in the stated order, and was dried with anhydrous magnesium sulfate. The resultant crude product was purified by column chromatography to provide 5.3 g of an N33 intermediate 1 (yield: 41%).

(2) Synthesis of N33 Intermediate 2

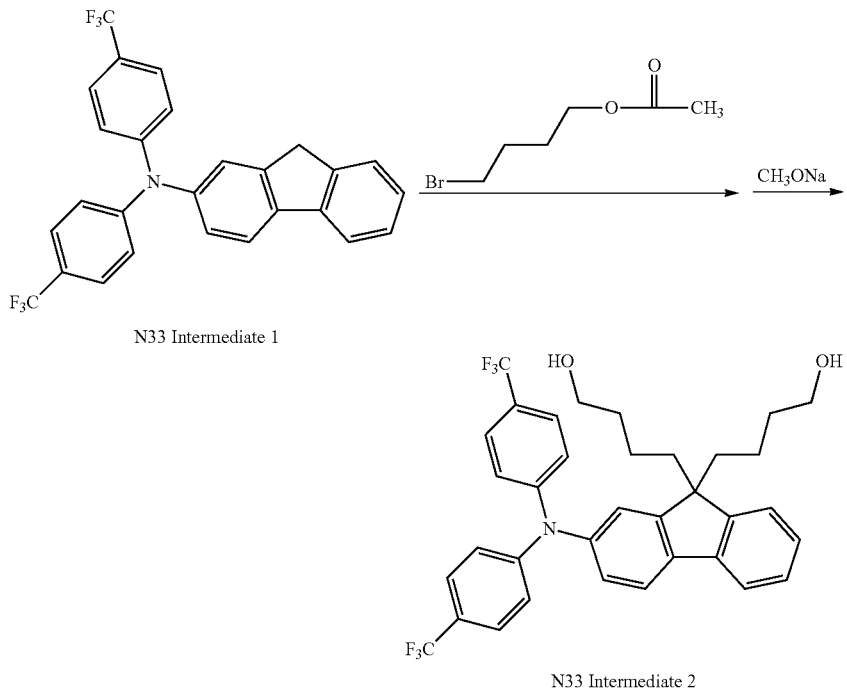

N33 Intermediate 1

N33 Intermediate 2

Under a nitrogen atmosphere, 5.0 g of the N33 intermediate 1 and 50 mL of N,N-dimethylacetamide were loaded into a 300-milliliter three-necked flask, and the mixture was stirred. After that, 3.58 g of sodium tert-butoxide was loaded into the mixture, and the whole was cooled to 5° C. A solution obtained by dissolving 5.35 g of 4-bromobutyl acetate in 12 mL of N,N-dimethylacetamide was dropped into the resultant over 30 minutes. After the dropping, the temperature of the mixture was increased to 20° C., and then the mixture was stirred at the temperature (20° C.) for 20 hours. After the stirring, the mixture was cooled to 5° C. Next, 2.87 g of sodium methoxide was loaded into the mixture, and the temperature of the whole was gradually increased to 20° C. After the temperature increase, the mixture was stirred at the temperature (20° C.) for 10 hours. After the stirring, the reaction liquid was loaded into ice water, and the organic layer was extracted with toluene. The resultant organic phase was washed with brine and water in the stated order, and was dried with anhydrous magnesium sulfate. The resultant crude product was purified by column chromatography to provide 2.6 g of an N33 intermediate 2 (yield: 40%). The structure of the product was identified by $^1$H-NMR.

$^1$H-NMR (CDCl$_3$): δ 0.69 (t, 2H), 1.36 (d, 4H), 1.62 (d, 4H), 1.96 (dd, 4H), 3.08 (dd, 4H), 7.10 (dd, 1H), 7.17 (dd, 4H), 7.22 (d, 1H), 7.32-7.40 (m, 2H), 7.43 (d, 1H), 7.51 (d, 4H), 7.68 (t, 2H)

(3) Synthesis of N33

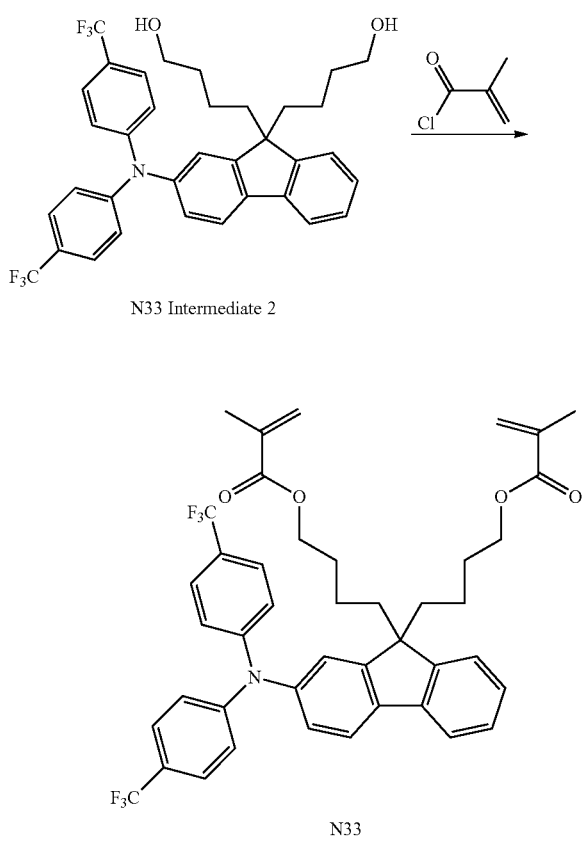

N33 Intermediate 2

N33

Under a nitrogen atmosphere, 2.0 g of the N33 intermediate 2, 70 mL of tetrahydrofuran, 0.12 g of MEHQ, and 1.8 mL of triethylamine were loaded into a 300-milliliter three-necked flask. The reaction vessel was cooled to 0° C., and 1.0 mL of methacryloyl chloride was dropped into the mixture. The reaction liquid was diluted with toluene, and then a 2 N aqueous solution of hydrochloric acid was used to terminate the reaction. The resultant organic layer was washed with an acidic aqueous solution and a basic aqueous solution. After that, the organic layer was dried with brine and anhydrous magnesium sulfate. The solvent was removed, and the resultant crude product was purified by silica gel chromatography. Thus, 1.33 g of the N33 was obtained (54%). The structure of the product was identified by $^1$H-NMR. In addition, the optical characteristics of the product are shown in Table 6.

$^1$H-NMR (CDCl$_3$): δ 1.79 (t, 6H), 1.41 (d, 4H), 1.73 (d, 4H), 2.12-2.19 (m, 4H), 3.22-3.29 (m, 4H), 5.43 (t, 2H), 5.80 (t, 2H), 6.91 (dd, 1H), 7.13 (dd, 1H), 7.22 (d, 4H), 7.30-7.38 (m, 2H), 7.43 (d, 1H), 7.54 (d, 4H), 7.67 (d, 2H)

Example 6

(Production of Compound Example N34)
(1) Synthesis of N34 Intermediate 1

Under a nitrogen atmosphere, 5.0 g of the N33 intermediate 1 and 50 mL of N,N-dimethylacetamide were loaded into a 300-milliliter three-necked flask, and the mixture was stirred. After that, 3.58 g of sodium tert-butoxide was loaded into the mixture, and the whole was cooled to 5° C. A solution obtained by dissolving 4.62 g of 2-bromoethyl acetate in 10 mL of N,N-dimethylacetamide was dropped into the resultant over 30 minutes. After the dropping, the temperature of the mixture was increased to 20° C., and then the mixture was stirred at the temperature (20° C.) for 20 hours. After the stirring, the mixture was cooled to 5° C. 2.87 g of sodium methoxide was loaded into the mixture, and the temperature of the whole was gradually increased to 20° C. After the temperature increase, the mixture was stirred at the temperature (20° C.) for 10 hours. After the stirring, the reaction liquid was loaded into ice water, and the organic layer was extracted with toluene. The resultant organic phase was washed with brine and water in the stated order, and was dried with anhydrous magnesium sulfate. The resultant crude product was purified by column chromatography to provide 1.8 g of an N34 intermediate 1 (yield: 30%). The structure of the product was identified by $^1$H-NMR.

$^1$H-NMR (CDCl$_3$): δ 0.69 (t, 2H), 2.25-2.37 (m, 4H), 3.09 (dd, 4H), 7.11 (dd, 1H), 7.16 (dd, 4H), 7.22 (d, 1H), 7.32-7.40 (m, 2H), 7.43 (d, 1H), 7.51 (d, 4H), 7.68 (t, 2H)

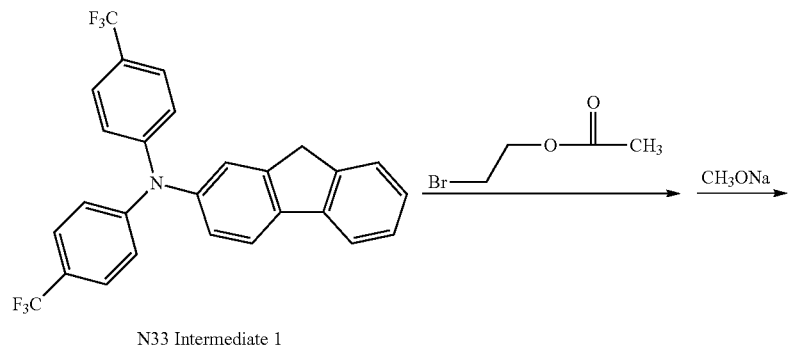

N33 Intermediate 1

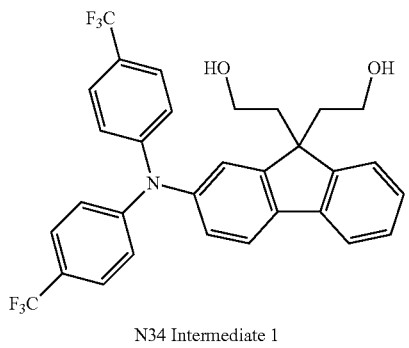

N34 Intermediate 1

(2) Synthesis of N34

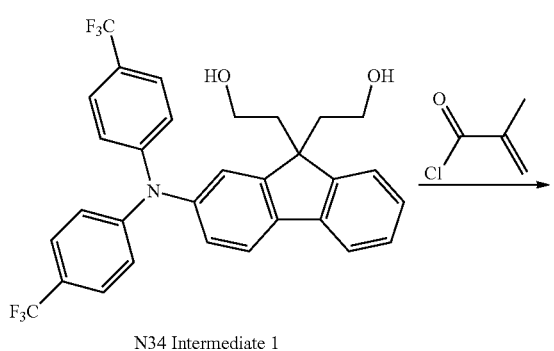

N34 Intermediate 1

N34

Under a nitrogen atmosphere, 1.7 g of the N34 intermediate 1, 60 mL of tetrahydrofuran, 0.11 g of MEHQ, and 1.7 mL of triethylamine were loaded into a 200-milliliter three-necked flask. The reaction vessel was cooled to 0° C., and 0.9 mL of methacryloyl chloride was dropped into the mixture. The reaction liquid was diluted with toluene, and then a 2 N aqueous solution of hydrochloric acid was used to terminate the reaction. The resultant organic layer was washed with an acidic aqueous solution and a basic aqueous solution. After that, the organic layer was dried with brine and anhydrous magnesium sulfate. The solvent was removed, and the resultant crude product was purified by silica gel chromatography. Thus, 1.20 g of the N34 was obtained (56%). The structure of the product was identified by $^1$H-NMR. In addition, the optical characteristics of the product are shown in Table 6.

$^1$H-NMR (CDCl$_3$): δ 1.79 (t, 6H), 2.30-2.37 (m, 2H), 2.40-2.49 (m, 2H), 3.46-3.51 (m, 2H), 3.62-3.67 (m, 2H), 5.43 (t, 2H), 5.82 (t, 2H), 6.91 (dd, 1H), 7.11 (dd, 1H), 7.22 (d, 4H), 7.31-7.37 (m, 2H), 7.43 (d, 1H), 7.52 (d, 4H), 7.66 (d, 2H)

Example 7

(Production of Compound Example N35)

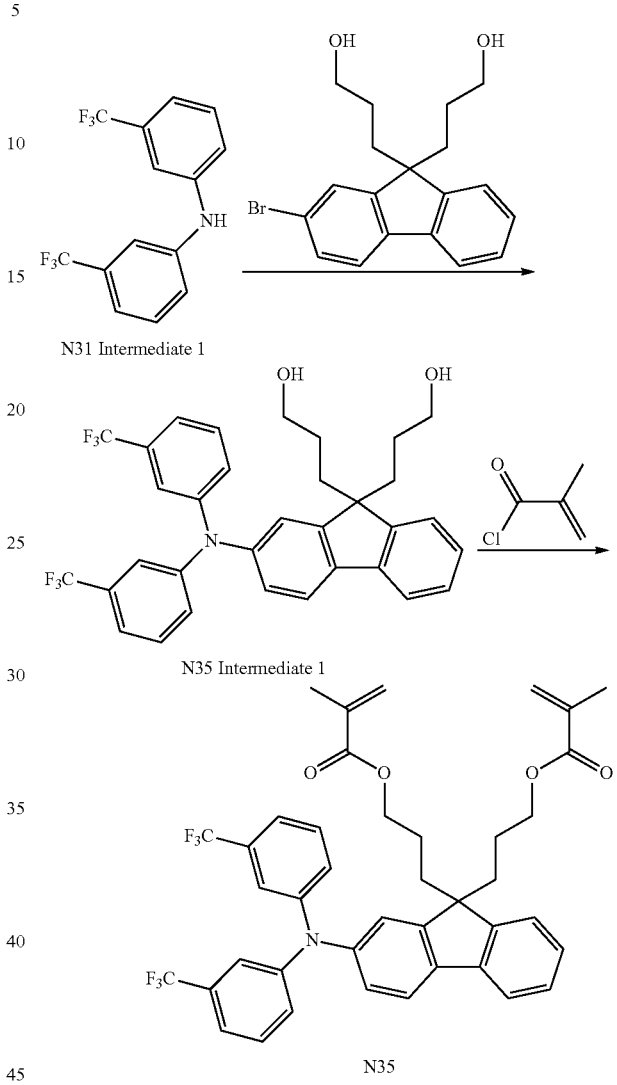

The same reactions and purifications as those of Example 3 were performed with the exception that an N35 intermediate 1 was obtained by changing 2-bromofluorene used in Example 3 to 3-[2-bromo-9-(3-hydroxy-propyl)-9H-fluoren-9-yl]-propan-1-ol. In addition, the optical characteristics of the product are shown in Table 6.

$^1$H-NMR (CDCl$_3$): δ 1.52 (d, 4H), 1.78 (s, 6H), 1.90 (d, 4H), 3.47-3.52 (m, 2H), 3.60-3.65 (m, 2H), 5.43 (t, 2H), 5.81 (t, 2H), 6.90 (dd, 1H), 7.10 (dd, 1H), 7.21 (d, 4H), 7.30-7.36 (m, 2H), 7.42 (d, 1H), 7.51 (d, 4H), 7.65 (d, 2H)

Example 8

(Production of Compound Example N40)

The same reactions and purifications as those of Example 3 were performed with the exception that 3-aminobenzotrifluoride, 3-bromobenzotrifluoride, and 4-bromobutyl acetate used in Example 3 were changed to 4-aminobenzonitrile, 2-bromo-m-xylene, and 2-bromoethyl acetate, respectively.

Example 9

(Production of Compound Example N23)

The same reactions and purifications as those of Example 2 were performed with the exception that 2-amino-9,9-dimethylfluorene, 4-bromobenzonitrile, and 4-bromobenzyl alcohol used in Example 2 were changed to 3,5-bis(trifluoromethyl)aniline, 2-bromo-9,9-di-n-octylfluorene, and 2-(4-bromophenyl)ethyl alcohol, respectively. In addition, the optical characteristics of the product are shown in Table 6.

Example 10

(Production of Compound Example N46)

The same reactions and purifications as those of Example 3 were performed with the exception that 3-bromobenzotrifluoride and 2-bromofluorene used in Example 3 were changed to 4-bromobenzyl alcohol and 3-[2-bromo-9-(3-hydroxy-propyl)-9H-fluoren-9-yl]-propan-1-ol, respectively. In addition, the optical characteristics of the product are shown in Table 6.

Example 11

(Production of Compound Example N2)

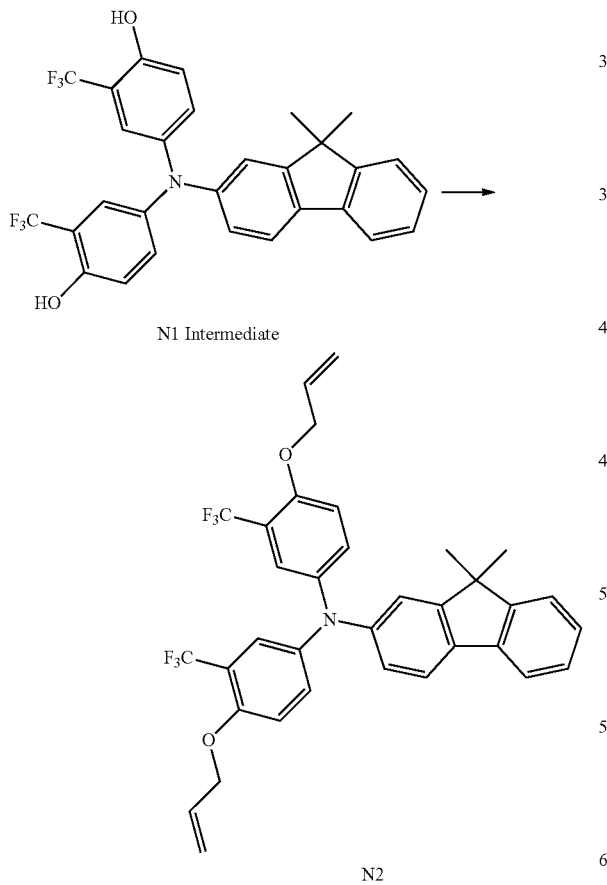

Under a nitrogen atmosphere, 60 ml of a solution of 0.4 g of sodium hydride (55%) in tetrahydrofuran was loaded into a 200-milliliter three-necked flask, and 2.0 g of the N1 intermediate was slowly added to the solution at 0° C., followed by stirring at the temperature for 1 hour. Next, 1.6 g of allyl bromide was added to the mixture to confirm that a reaction occurred, and then a saturated aqueous solution of ammonium chloride was used to terminate the reaction. The organic phase was extracted with ethyl acetate, and was then dried with anhydrous magnesium sulfate. A crude product obtained by concentrating the organic phase was purified by silica gel chromatography to provide 1.48 g of the N2 (yield: 77%). The structure of the product was identified by $^1$H-NMR. In addition, the optical characteristics of the product are shown in Table 6.

$^1$H-NMR (CDCl$_3$): δ 1.54 (s, 6H), 4.55-4.62 (m, 4H), 5.43 (d, 2H), 5.88 (t, 2H), 6.46 (t, 2H), 7.10 (d, 1H), 7.27-7.42 (m, 5H), 7.62-7.69 (m, 4H), 7.78 (d, 1H), 8.10 (d, 1H), 8.17 (d, 1H)

Example 12

(Production of Compound Example N36)

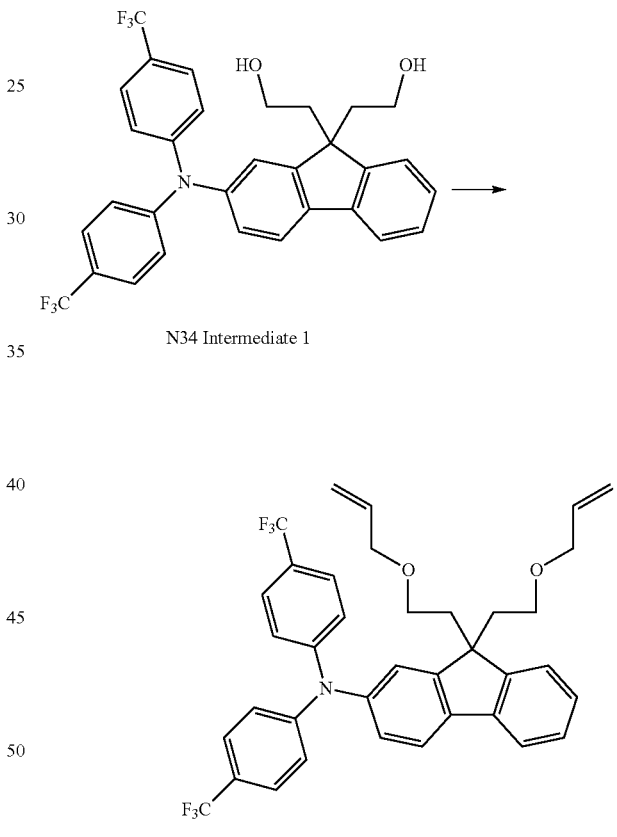

The same reaction and purification as those of Example 11 were performed with the exception that the N1 intermediate of Example 11 was changed to the N34 intermediate 1.

Comparative Example 1

A comparative example compound R1 was synthesized, and its refractive index, dispersion characteristic (Abbe number (vd)), secondary dispersion characteristic (θg,F), and transmittance were compared. The results are shown in Table 6.

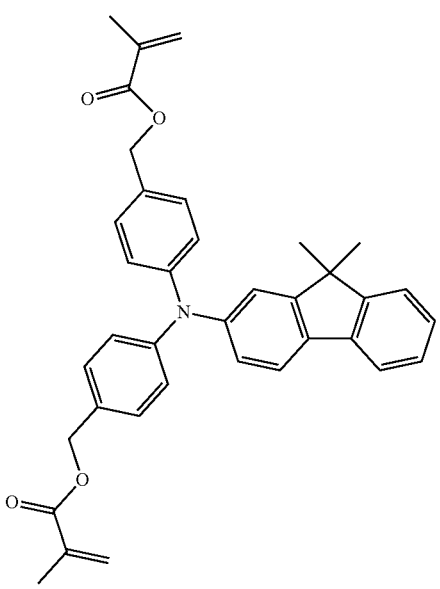 [SMILES: C=C(C)C(=O)OCc1ccc(N(c2ccc(COC(=O)C(=C)C)cc2)c2ccc3c(c2)C(C)(C)c2ccccc2-3)cc1]

Comparative Example Compound R1

Comparative Example 2

A comparative example compound R2 was synthesized, and its refractive index, dispersion characteristic (Abbe number (vd)), secondary dispersion characteristic (θg,F), and transmittance were compared. The results are shown in Table 6.

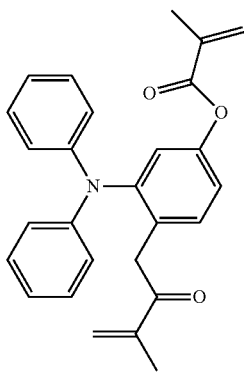 [SMILES: C=C(C)C(=O)Cc1ccc(OC(=O)C(=C)C)cc1N(c1ccccc1)c1ccccc1]

Comparative Example Compound R2

(Evaluation)

A refractive index was measured with an Abbe refractometer (manufactured by Kalnew Optical Industrial Co., Ltd.).

With regard to a transmittance, two kinds of films having different optical path lengths were molded, and their transmittances were each measured with a spectrophotometer U-4000 (trade name) manufactured by Hitachi High-Technologies Corporation, followed by their conversion into internal transmittances (500 μm) at 450 nm. The results are shown in Table 6.

TABLE 6

|  | nd | vd | θg, F | Transmittance |
|---|---|---|---|---|
| Example 1 | 1.64 | 18.9 | 0.79 | 96 |
| Example 2 | 1.77 | 19.2 | 0.80 | 82 |
| Example 3 | 1.60 | 16.5 | 0.79 | 95 |
| Example 4 | 1.58 | 19.0 | 0.79 | 98 |
| Example 5 | 1.60 | 15.6 | 0.82 | 98 |
| Example 6 | 1.58 | 18.5 | 0.77 | 99 |
| Example 7 | 1.59 | 17.4 | 0.78 | 96 |
| Example 8 | 1.78 | 19.3 | 0.81 | 95 |
| Example 9 | 1.66 | 17.7 | 0.79 | 85 |
| Example 10 | 1.61 | 19.5 | 0.78 | 92 |
| Example 11 | 1.62 | 18.1 | 0.80 | 90 |
| Example 12 | 1.61 | 16.6 | 0.78 | 93 |
| Comparative Example 1 | 1.78 | 21.0 | 0.78 | 72 |
| Comparative Example 2 | 1.66 | 28.6 | 0.69 | 85 |

According to the present invention, the triarylamine compound having a characteristic in that the dispersion characteristic (Abbe number (vd)) of refractive indices is high and the secondary dispersion characteristic (θg,F) thereof is high (high θg,F characteristic), that is, a chromatic aberration-correction function is high, and the material and the optical element each using the compound can be provided.

In addition, according to the present invention, the optical material having a characteristic in a range A in FIG. 1 can be provided. The use of the optical element molded out of the optical material can efficiently remove a chromatic aberration. Accordingly, an optical system can be further reduced in weight and size.

The optical element, material, optical apparatus, and triarylamine compound of the present invention each have a characteristic in that the dispersion characteristic (Abbe number (vd)) of refractive indices is high and the secondary dispersion characteristic (θg,F) thereof is high (abnormal dispersion characteristic), that is, a chromatic aberration-correction function is high. Accordingly, the optical element, the material, the optical apparatus, and the triarylamine compound may each be suitably utilized in an apparatus having a plurality of lenses, such as a camera lens.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An optical element comprising an optical member including a polymer obtained by subjecting a compound represented by general formula (1) to homopolymerization or copolymerization:

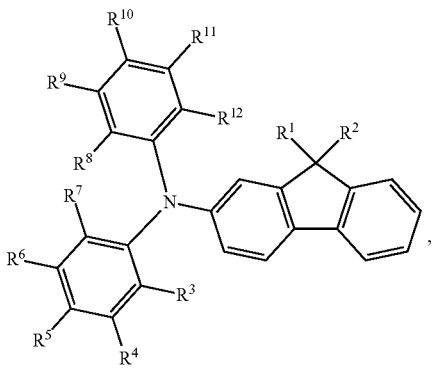

(1)

wherein, in the general formula (1), $R^1$ and $R^2$ are each independently selected from a substituted or unsubstituted alkyl group having 1 to 10 carbon atoms, and a substituted or unsubstituted alkylene group having 1 to 8 carbon atoms, the alkylene group having a polymerizable functional group, and $R^3$ to $R^{12}$ are each independently selected from a hydrogen atom, a cyano group, a trifluoromethyl group, a substituted or unsubstituted alkyl group, a substituted or unsubstituted alkylene group having a polymerizable functional group, and a polymerizable functional group, provided that at least one of $R^3$ to $R^{12}$ represents an electron-withdrawing group, and at least one of $R^1$ to $R^{12}$ has a polymerizable functional group.

2. The optical element according to claim 1, wherein the polymerizable functional group comprises an acryloyloxy group, a methacryloyloxy group, a vinyl group, or an epoxy group.

3. The optical element according to claim 1, wherein at least one of $R^5$, $R^6$, $R^9$, or $R^{10}$ represents an electron-withdrawing group, and the electron-withdrawing group comprises a cyano group or a trifluoromethyl group.

4. An optical apparatus comprising the optical element according to claim 1.

5. The optical apparatus according to claim 4, wherein the optical element comprises a lens and the optical apparatus comprises a camera.

6. The optical element according to claim 1, wherein a content of the polymer obtained by subjecting the compound represented by the general formula (1) to homopolymerization or copolymerization in the optical member is 1.0 wt.% to 99 wt.%.

7. The optical element according to claim 1, wherein a content of the polymer obtained by subjecting the compound represented by the general formula (1) to homopolymerization or copolymerization in the optical member is 50 wt.% to 99 wt.%.

8. The optical element according to claim 1, wherein the optical member contains a resin, and
wherein a content of the resin in the optical member is 0.01 wt.% to 99 wt.%.

9. The optical element according to claim 1, wherein the optical member contains a resin, and
wherein a content of the resin in the optical member is 0.01 wt.% to 50 wt.%.

10. A material comprising a polymer obtained by subjecting a compound represented by general formula (1) to homopolymerization or copolymerization:

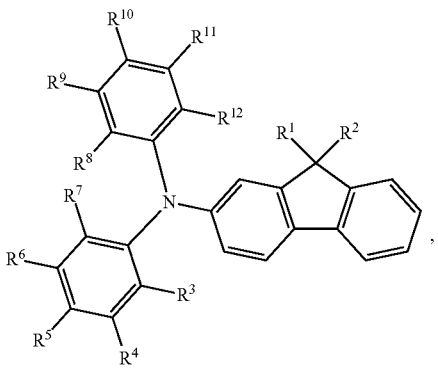

(1)

wherein, in the general formula (1), $R^1$ and $R^2$ are each independently selected from a substituted or unsubstituted alkyl group having 1 to 10 carbon atoms, and a substituted or unsubstituted alkylene group having 1 to 8 carbon atoms, the alkylene group having a polymerizable functional group, and $R^3$ to $R^{12}$ are each independently selected from a hydrogen atom, a cyano group, a trifluoromethyl group, a substituted or unsubstituted alkyl group, a substituted or unsubstituted alkylene group having a polymerizable functional group, and a polymerizable functional group, provided that at least one of $R^3$ to $R^{12}$ represents an electron-withdrawing group, and at least one of $R^1$ to $R^{12}$ has a polymerizable functional group.

11. The material according to claim 10, wherein the polymerizable functional group comprises an acryloyloxy group, a methacryloyloxy group, a vinyl group, or an epoxy group.

12. The material according to claim 10, wherein at least one of $R^5$, $R^6$, $R^9$, or $R^{10}$ represents an electron-withdrawing group, and the electron-withdrawing group comprises a cyano group or a trifluoromethyl group.

13. A compound represented by general formula (1):

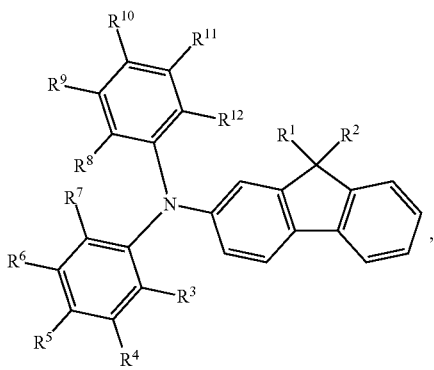

(1)

wherein, in the general formula (1), $R^1$ and $R^{12}$ are each independently selected from a substituted or unsubstituted alkyl group having 1 to 10 carbon atoms, and a substituted or unsubstituted alkylene group having 1 to 8 carbon atoms, the alkylene group having a polymerizable functional group, and $R^3$ to $R^{12}$ are each independently selected from a hydrogen atom, a cyano group, a trifluoromethyl group, a substituted or unsubstituted alkyl group, a substituted or unsubstituted alkylene group having a polymerizable functional group, and a polymerizable functional group, provided that at least one of $R^3$ to $R^{12}$ represents an electron-withdrawing group, and at least one of $R^1$ to $R^{12}$ has a polymerizable functional group.

14. The compound according to claim 13, wherein the polymerizable functional group comprises an acryloyloxy group, a methacryloyloxy group, a vinyl group, or an epoxy group.

15. The compound according to claim 13, wherein at least one of $R^5$, $R^6$, $R^9$, or $R^{10}$ represents an electron-withdrawing group, and the electron-withdrawing group comprises a cyano group or a trifluoromethyl group.

* * * * *